(12) United States Patent
Nagasawa et al.

(10) Patent No.: US 10,451,640 B2
(45) Date of Patent: Oct. 22, 2019

(54) IRON (II) ION DETECTION AGENT AND DETECTION METHOD USING SAME

(71) Applicant: Metallogenics Co., Ltd., Chiba, Chiba (JP)

(72) Inventors: Hideko Nagasawa, Gifu (JP); Tasuku Hirayama, Gifu (JP)

(73) Assignee: Cellspect Co., Ltd., Morioka-shi, Iwate (JP)

( * ) Notice: Subject to any disclaimer, the term of this patent is extended or adjusted under 35 U.S.C. 154(b) by 230 days.

(21) Appl. No.: 15/111,919

(22) PCT Filed: Jan. 16, 2015

(86) PCT No.: PCT/JP2015/051151
§ 371 (c)(1),
(2) Date: Jul. 15, 2016

(87) PCT Pub. No.: WO2015/108172
PCT Pub. Date: Jul. 23, 2015

(65) Prior Publication Data
US 2016/0356796 A1    Dec. 8, 2016

(30) Foreign Application Priority Data

Jan. 17, 2014 (JP) .................. 2014-007140

(51) Int. Cl.
*G01N 31/22* (2006.01)
*G01N 33/18* (2006.01)
(Continued)

(52) U.S. Cl.
CPC .......... *G01N 33/84* (2013.01); *C07D 311/82* (2013.01); *C07D 493/10* (2013.01); *C09B 11/24* (2013.01);
(Continued)

(58) Field of Classification Search
None
See application file for complete search history.

(56) References Cited

U.S. PATENT DOCUMENTS

2001/0001800 A1   5/2001  Nagano et al.
2003/0162298 A1   8/2003  Nagano et al.
(Continued)

FOREIGN PATENT DOCUMENTS

JP   2004-101389   4/2004
JP   2013-193990   9/2013
(Continued)

OTHER PUBLICATIONS

Weerasinghe, A.J. "Rhodamine based turn-ON dual sensor for Fe3+ and Cu2+," Tetrahedron Letters, vol. 52, Issue 43, Oct. 26, 2011, pp. 5648-5651 (Year: 2011).*

(Continued)

*Primary Examiner* — Christopher Adam Hixson
*Assistant Examiner* — Michelle Adams
(74) *Attorney, Agent, or Firm* — McCarter & English, LLP

(57) ABSTRACT

An Fe(II) ion detection agent, and related method, capable of fluorescently detecting Fe(II) ions quickly with high (Continued)

sensitivity is disclosed. The Fe(II) ion detection agent can be a compound represented by formula (I) (fluorescence probe):

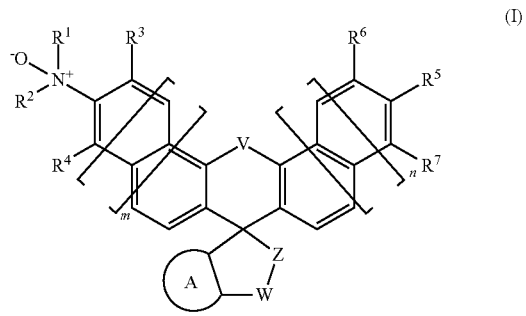

(I)

wherein $R^1$ and $R^2$ represent lower alkyl; $R^3$ and $R^4$ represent hydrogen; $R^5$ represents hydrogen, hydroxyl, or a group represented by formula (A): —$NR^{51}R^{52}$ wherein $R^{51}$ and $R^{52}$ represent lower alkyl; $R^6$ and $R^7$ represent hydrogen; ring A represents an aromatic ring; V represents O or $SiR^{10}R^{11}$ wherein $R^{10}$ and $R^{11}$ are the same or different and represent, hydrogen or lower alkyl; W represents $CH_2$, CO; Z represents O; m and n are the same or different and represent 0 or 1. The agent can be combined with a compound having at least three coordinating positions.

9 Claims, 9 Drawing Sheets

(51) Int. Cl.
 G01N 33/84 (2006.01)
 C07D 493/10 (2006.01)
 C07D 311/82 (2006.01)
 G01N 21/64 (2006.01)
 C09B 11/24 (2006.01)
 G01N 33/52 (2006.01)
(52) U.S. Cl.
 CPC ......... *G01N 21/6428* (2013.01); *G01N 31/22* (2013.01); *G01N 33/1813* (2013.01); *G01N 2021/6439* (2013.01)

(56) References Cited

U.S. PATENT DOCUMENTS

2005/0064308 A1 3/2005 Nagano et al.
2009/0137612 A1 5/2009 Waugh

FOREIGN PATENT DOCUMENTS

WO 99/01447 1/1999
WO 01/62755 8/2001
WO 2004/041151 5/2004

OTHER PUBLICATIONS

Niwa, M. et al. "A new class of high-contrast Fe(II) selective fluorescent probes based on spirocyclized scaffolds for visualization of intracellular labile iron delivered by transferrin," Org. Biomol. Chem., 2014, 12, 6590-6597; first published on Jun. 3, 2014 (Year: 2014).*
Hirayama, T. et al. "A highly selective turn-on fluorescent probe for iron(II) to visualize labile iron in living cells," Chem. Sci., 2013, 4, 1250-1256; First published on Dec. 20, 2012 (Year: 2012).*
Bartzokis, George, et al., "In Vivo Evaluation of Brain Iron in Alzheimer's Disease and Normal Subjects Using MRI", Biological Psychiatry, 1994, vol. 35, pp. 480-487.
Cuajungco, Math P., et al., "Metal Chelation as a Potential Therapy for Alzheimer's Disease", Annals New York Academy of Sciences, 2000, vol. 920, pp. 292-304.
Dexter, D.T., et al., "Increased Nigral Iron Content and Alterations in Other Metal Ions Occurring in Brain in Parkinson's Disease", Journal of Neurochemistry, 1989, vol. 52, No. 6, pp. 1830-1836.
Toyokuni, Shinya, "Elucidation of Asbestos-induced Carcinogenesis and Its Application to Prevention, Diagnosis and Treatment in Relation to Iron", Japanese Journal of Lung Cancer, Aug. 20, 2009, vol. 49, No. 4., pp. 362-367.
Nishina, Sohji, et al., "Hepatitis C Virus Protein and Iron Overload Induce Hepatic Steatosis Through the Unfolded Protein Response in Mice", Liver International, 2010, vol. 30, No. 5, pp. 683-692.
Kikuchi, Kazuya, et al., "Zinc Sensing for Cellular Application", Current Opinion in Chemical Biology, 2004, vol. 8, pp. 182-191.
Que, Emily L., et al., "Metals in Neurobiology: Probing Their Chemistry and Biology with Molecular Imaging", Chemical Reviews, 2008, vol. 108, No. 5, pp. 1517-1549.
Fakih, Sarah, et al., "Targeting the Lysosome: Fluorescent Iron (III) Chelators to Selectively Monitor Endosomal/Lysosomal Labile Iron Pools", Journal of Medicinal Chemistry, 2008, vol. 51, No. 15, pp. 4539-4552.
Rauen, Ursula, et al., "Assessment of Chelatable Mitochondrial Iron by Using Mitochondrion-Selective Fluorescent Iron Indicators with Different Iron-Binding Affinities", ChemBioChem, 2007, vol. 8, pp. 341-352.
Hirayama, Tasuku, et al., "Development of Fluorescent Probes for Fe(II) Ion Based on N-oxide Chemistry", Japanese Society for Chemical Biology, 8th Annual Meeting, Conference Summary, 2013, p. 159.
Niwa, Masato, et al., "Development of Iron (II) Selective Fluorescence Probe Based on Controlled Spirocyclization", 7th Bio-related Chemistry Symposium, Conference Summary, 2013, p. 101.
Hirayama, Tasuku, et al., "Development of Selective Fluorescent Probes for Fe (II) and their Application", 93rd Annual Meeting of the Chemical Society of Japan in Spring Gakkai Yoshishu, 2013, 2E3-49, pp. 1-5.
Nakata, Eiji, et al., "Design of a Bioreductively-Activated Fluorescent pH Probe for Tumor Hypoxia Imaging", Biorganic & Medicinal Chemistry, 2009, vol. 17, pp. 6952-6958.
Peng, Tao, et al., "Construction of a Library of Rhodol Fluorophores for Developing New Fluorescent Probes", Organic Letters, 2010, vol. 12, No. 3, pp. 496-499.
Grimm, Jonathan B., et al., "Synthesis of Rhodamines from Fluoresceins Using Pd-Catalyzed C—N Cross-Coupling", Organic Letters, 2011, vol. 13, No. 24, pp. 6354-6357.
Kamiya, Mako, et al., "B-Galactosidase Fluorescence Probe with Improved Cellular Accumulation Based on a Spirocyclized Rhodol Scaffold", Journal of the American Chemical Society, 2011, vol. 133, pp. 12960-12963.
Xuan, Weimin, et al., A FRET-based Ratiometric Fluorescent and Colorimetric Probe for the Facile Detection of Organophosphonate Nerve Agent Mimic DCP, Chemical Communications, 2013, vol. 49, pp. 10474-10476.
Wang, Baogang, et al., "A General Approach to Spirolactonized Si-Rhodamines", Chemical Communications, 2014 vol. 50, pp. 14374-14377.
Best, Quinn A., et al., "Design and Investigation of a Series of Rhodamine-Based Fluorescent Probes for Optical Measurements of pH", Organic Letters, 2010, vol. 12, No. 14, pp. 3219-3221.
Woodroofe, Carolyn C., et al., "Synthesis of Isomerically Pure Carboxylate- and Sulfonate-Substituted Xanthene Fluorophores", Tetrahedron, 2005, vol. 61, pp. 3097-3105.

* cited by examiner

IRON (II) ION DETECTION AGENT AND DETECTION METHOD USING SAME

TECHNICAL FIELD

CROSS-REFERENCE TO RELATED APPLICATIONS

This application is a national stage application filed under 35 USC 371 of PCT/JP2015/051151, filed Jan. 16, 2015, which claims the benefit of Japanese Patent Application No. 2014-007140, filed Jan. 17, 2014, each of which are incorporated herein, in entirety, by reference.

The present invention relates to an Fe(II) ion detection agent. Specifically, the present invention relates to an Fe(II) ion detection agent capable of selectively measuring Fe(II) ions in a test tube or in living cells with high sensitivity.

BACKGROUND ART

Iron is the most abundant transition metal species in the human body and is involved in various life phenomena, including oxygen transport and electron transfer in the respiratory system. However, abnormal levels of iron in the body have been suggested as being associated with serious diseases, such as cancer, Alzheimer's disease, and Parkinson's disease. In particular, Fe(II) ions, representing the large part of in vivo free iron ions, have been suspected of contributing to asbestos cancer or hepatitis C because of their high potential for generating reactive oxygen species (e.g., Patent Literature 1 and 2, and Non-patent Literature 1 to 5). A fluorescence probe capable of selectively detecting Fe(II) ions in living cells or living tissues, and at the same time acutely detecting a change in the concentration, when such a probe is developed, will be a tremendously important technique, for example, in research of diseases and life phenomena associated with Fe(II) ions, as well as pharmaceutical development.

Recent years have seen active development of fluorescence probes for labeling biomolecules, ions, and the like. For example, many fluorescence probes that have a fluorophore as a frame structure, such as fluorescein and rhodamine, have been reported (e.g., Patent Literature 3 and 4 and Non-patent Literature 6 and 7).

Fluorescence probes for detecting iron ions reported so far include a quenched iron ion detecting probe (e.g., Non-patent Literature 8 and 9). However, due to its low detection sensitivity or selectivity to iron ions, it is difficult to acutely detect a change in the concentration by using this probe.

Patent Literature 5 reports a fluorescence probe for measuring aluminium ions and/or ferric ion ions. However, the target of the probe is Fe(III) ions, not Fe(II) ions. Moreover, the selectivity of metal ions is unsatisfactory with this probe.

To solve the problems, Patent Literature 6 reports an Fe(II) ion detection fluorescence probe that has an N-oxide moiety (e.g., RhoNox-1; see FIG. 1). This fluorescence probe exploits the following characteristics; i.e., the N-oxide moiety reacts with an Fe(II) ion to thereby undergo deoxygenation, thus increasing fluorescence. Such a fluorescence probe producing a fluorescence-emission response to Fe(II) ions is very creative, making a clear departure from traditional fluorescence probes that produce a quenched response. The fluorescence probe is also excellent in detection sensitivity and selectivity to Fe(II) ions.

Non-patent Literature 10 to 12 report fluorescence probes that are improved versions of the fluorescence probe disclosed in Patent Literature 6 (e.g., RhoNox-1). Specifically, the fluorescence probes of Patent Literature 10 to 12 are compounds obtained by replacing the carboxyl in the rhodamine frame structure of RhoNox-1 with hydroxyl (e.g., HMRhoNox-M and HMRhoNox-E in FIG. 1).

CITATION LIST

Patent Literature

Patent Literature 1: JP2011-79834A
Patent Literature 2: US2009/137612A
Patent Literature 3: WO01/62755
Patent Literature 4: WO99/01447
Patent Literature 5: JP2004-101389A
Patent Literature 6: JP2013-193990A

Non-Patent Literature

Non-patent Literature 1: Bartzokis, G. et al. In vivo evaluation of brain iron in Alzheimer's disease and normal subjects using MRI. Biol. Psychiatry 35, 480-487 (1994)
Non-patent Literature 2: Cuajungco, M. P. et al. Metal chelation as a potential therapy for Alzheimer's disease. Ann. N. E. Acad. Sci. 920: 292-304 (2000)
Non-patent Literature 3: Dexter, D. T. et al. Increased Nigral Iron Content and Alterations in Other Metal Ions Occurring in Brain in Parkinson's Disease. J. Neurochem. 52, 1830-1836 (1989)
Non-patent Literature 4: Toyokuni, S. Elucidation of Asbestos-induced Carcinogenesis and Its Application to Prevention, Diagnosis and Treatment in Relation to Iron. Japan. J. of Lung Cancer 49(4), 362-367 (2009)
Non-patent Literature 5: Nishina S., Korenaga M., Hidaka I., Shinozaki A., Sakai A., Gondo T., Tabuchi M., Kishi F., Hino K. Hepatitis C virus protein and iron overload induce hepatic steatosis through the unfolded protein response in mice. Liver Int. 30(5) 683-92 (2010)
Non-patent Literature 6: Kikuchi, K., Komatsu, K. & Nagano, T. Zinc sensing for cellular application. Current opinion in chemical biology 8, 182-91 (2004)
Non-patent Literature 7: Que, E. L., Domaille, D. W. & Chang, C. J. Metals in neurobiology: probing their chemistry and biology with molecular imaging. Chemical reviews 108, 1517-49 (2008)
Non-patent Literature 8: Fakih, S. et al. Targeting the lysosome: fluorescent iron(III) chelators to selectively monitor endosomal/lysosomal labile iron pools. Journal of medicinal chemistry 51, 4539-52 (2008)
Non-patent Literature 9: Rauen, U. et al. Assessment of Chelatable Mitochondrial Iron by Using Mitochondrion-Selective Fluorescent Iron Indicators with Different Iron-Binding Affinities. ChemBioChem 8, 341-352 (2007)
Non-patent Literature 10: Japanese Society for Chemical Biology, 8th Annual Meeting (2013), Conference Summary, page 159
Non-patent Literature 11: 7th Bio-related Chemistry Symposium (2013), Conference Summary, page 101
Non-patent Literature 12: 93rd Annual Spring Meeting of the Chemical Society of Japan (2013), Conference Summary, Presentation No. 2E3-49

SUMMARY OF INVENTION

Technical Problem

Patent Literature 6 reports a fluorescence probe excellent in detection sensitivity and selectivity to Fe(II) ions. However, the rate of response to Fe(II) ions is not necessarily satisfactory. To develop applications of the probe in, for example, clinical diagnostics, detection kits, and automatic analyzers, an Fe(II) ion detection agent with faster fluorescence response performance has been desired.

An object of the present invention is to provide an Fe(II) ion detection agent capable of fluorescently detecting Fe(II) ions with higher sensitivity, faster than the fluorescence probe disclosed in Patent Literature 6, and to provide a detection method using the agent.

Solution to Problem

The present inventors conducted extensive research to achieve the object and found that allowing an aminoacetic acid based-chelate compound, such as nitrilotriacetic acid (NA) and ethylenediaminetetraacetic acid (EDTA), to be present together with the Fe(II) ion-selective fluorescence probe disclosed in Patent Literature 6 can significantly increase the response rate and the contrast of fluorescent response of the Fe(II) ion fluorescence probe. More specifically, the inventors found that the fluorescent response of the fluorescence probe disclosed in Patent Literature 6 can be more highly sensitive to Fe(II) ions. The inventors conducted further research on the basis of the findings and completed the present invention.

The present invention provides the following Fe(II) ion detection agent.

Item 1

An Fe(II) ion detection agent comprising a compound represented by formula (I) (fluorescence probe):

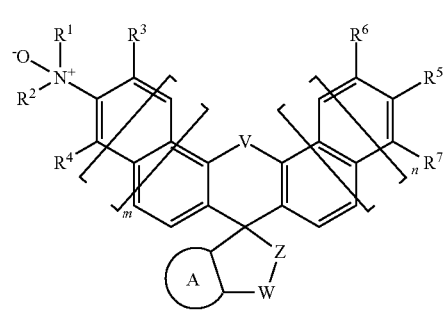

wherein $R^1$ and $R^2$ are the same or different and represent lower alkyl, carboxy lower alkyl, aryl, or aryl lower alkyl;

$R^3$ and $R^4$ are the same or different and represent hydrogen, halogen, or lower alkyl;

$R^1$ and $R^2$ may be taken together with the nitrogen atom to which they are attached to form a pyrrolidine ring, a piperidine ring, a morpholine ring, or an optionally substituted piperazine ring;

$R^1$ and $R^3$ may be taken together to form trimethylene;

$R^2$ and $R^4$ may be taken together to form trimethylene;

$R^5$ represents hydrogen, optionally protected hydroxyl, lower alkoxy, or a group represented by formula (A): —$NR^{51}R^{52}$ wherein $R^{51}$ and $R^{52}$ are the same or different and represent lower alkyl, carboxy lower alkyl, aryl, or aryl lower alkyl, or $R^{51}$ and $R^{52}$ may be taken together with the nitrogen atom to which they are attached to form a pyrrolidine ring, a piperidine ring, a morpholine ring, or an optionally substituted piperazine ring;

$R^6$ and $R^7$ are the same or different and represent hydrogen, halogen, or lower alkyl;

when $R^5$ is the group represented by formula (A), $R^{51}$ and $R^{52}$ may be taken together to form trimethylene, or $R^{52}$ and $R^7$ may be taken together to form trimethylene;

ring A represents an optionally substituted aromatic ring or an optionally substituted heteroaromatic ring;

V represents O or $SiR^{10}R^{11}$ wherein $R^{10}$ and $R^{11}$ are the same or different and represent hydrogen or lower alkyl;

W represents $CH_2$, CO, or $S(O)_p$;

Z represents O or $NR^9$ wherein $R^9$ represents hydrogen or alkyl;

m and n are the same or different and represent 0 or 1; and p represents 1 or 2, in combination with a compound having at least three coordinating positions.

Item 2

The Fe(II) ion detection agent according to Item 1, wherein the compound having at least three coordinating positions has the same or different at least three coordinating positions selected from the group consisting of amino, hydroxyl, carboxyl, a phosphonic acid group, and a nitrogen-containing heteroaromatic ring.

Item 3

The Fe(II) ion detection agent according to Item 1 or 2, wherein the compound having at least three coordinating positions is iminodiacetic acid (IDA), nitrilotriacetic acid (NTA), N,N,N',N'-ethylenediaminetetraacetic acid (EDTA), 1,3-propanediamine tetraacetic acid (PDTA), diethylenetriamine pentaacetic acid (DTPA), hydroxyethyl ethylenediamine triacetic acid (HEDTA), triethylenetetraamine-hexaacetic acid (TTHA), 1,2-diaminocyclohexane tetraacetic acid (CyDTA), glycol ether diamine tetraacetic acid (GEDTA or EGTA), N,N-bis(2-hydroxybenzyl)ethylenediamine diacetic acid (HBED), ethylenediamine dipropionic acid (EDDP), ethylenediamine diacetic acid (EDDA), ethylenediamine disuccinic acid (EDDS), 1,3-diamino-2-hydroxypropane tetraacetic acid (DPTA-OH), dihydroxyethyl glycine (DHEG), hexamethylenediamine tetraacetic acid (HDTA), hydroxyethyl iminodiacetic acid (HIDA), diaminopropane tetraacetic acid (Methyl-EDTA), nitrilotripropionic acid (NTP), L-glutamic acid diacetic acid (GLDA), O,O'-bis-2-aminophenyl-N,N,N',N'-tetraacetic acid (BAPTA), ethylenediamine tetrakis(methylene phosphonic acid) (EDTPO), nitrilotris(methylene phosphonic acid) (NTPO), hydroxyethylidene diphosphonic acid (HEDP), phosphonobutane tricarboxylic acid (PBTC), tris(2-pyridylmethyl)amine (TPA), dipicolylamine (DPA), o-aminophenol-N,N,O-triacetic acid (APTRA), porphyrin or its derivative, phthalocyanine or its derivative, 1,4,7-triazacyclononane (TACN), 1,4,7,10-tetra-azacyclo-dodecane (CYCL), 1,4,8,11-tetra-azacyclo-tetradecane (CYCLAM), or their salt.

Item 4

The Fe(II) ion detection agent according to any one of Items 1 to 3, wherein ring A in formula (I) is represented by formula (a):

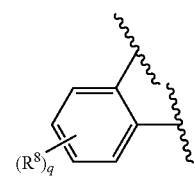

wherein Re represents optionally protected hydroxyl, lower alkoxy, halogen, carboxyl, lower alkoxycarbonyl, —N=C=O, —N=C=S, sulfo, or active ester; q represents 0, 1, 2 or 3; and when q is 2 or 3, $R^8$ may be the same or different.

Item 5

The Fe(II) ion detection agent according to any one of Items 1 to 4,
wherein $R^1$ and $R^2$ are the same or different and represent $C_{1-6}$ alkyl;
$R^1$ and $R^2$ may be taken together with the nitrogen atom to which they are attached to form a morpholine ring, or an optionally substituted piperazine ring;
$R^1$ and $R^4$ represents hydrogen, or
$R^1$ and $R^3$ may be taken together to form trimethylene;
$R^3$ and $R^4$ may be taken together to form trimethylene;
$R^5$ represents optionally protected hydroxyl or a group represented by formula (A): —$NR^{51}R^{52}$; when $R^5$ is the group represented by formula (A), $R^{51}$ and $R^{52}$ are the same or different and represent $C_{1-6}$ alkyl;
$R^6$ and $R^7$ represent hydrogen; or
$R^{51}$ and $R^6$ may be taken together to form trimethylene;
$R^{52}$ and $R^7$ may be taken together to form trimethylene;
q is 0; W is $CH_2$ or CO; Z is O; m is 0; and n is 0.

Item 6

The Fe(II) ion detection agent according to any one of Items 1 to 5, wherein $R^1$ and $R^2$ are the same or different and represent $C_{1-3}$ alkyl; $R^3$ and $R^4$ represent hydrogen; $R^5$ represents optionally protected hydroxyl or a group represented by formula (A): —$NR^{51}R^{52}$; when $R^5$ is the group represented by formula (A), $R^{51}$ and $R^{52}$ are the same or different and represent $C_{1-3}$ alkyl; $R^6$ and $R^7$ represent hydrogen; q is 0; W is $CH_2$ or CO; Z is O; m is 0; and n is 0.

Item 7

The Fe(II) ion detection agent according to any one of Items 1 to 6, wherein the compound represented by formula (I) (fluorescence probe) and the compound having at least three coordinating positions are mixed.

Item 8

The Fe(II) ion detection agent according to any one of Items 1 to 6 that is in the form of a kit comprising a container containing the compound represented by formula (I) (fluorescence probe) and a container containing the compound having at least three coordinating positions.

Item 9

A method for detecting Fe(II) ions, comprising the steps of:
(1) mixing a specimen containing Fe(II) ions with the Fe(II) ion detection agent according to any one of Items 1 to 8; and
(2) measuring a fluorescence spectrum of the obtained mixture.

Item 10

A method for increasing detection sensitivity to Fe(II) ions, comprising the steps of:
(1) mixing a specimen containing Fe(II) ions with the Fe(II) ion detection agent according to any one of Items 1 to 8; and
(2) measuring a fluorescence spectrum of the obtained mixture.

Item 11

A method for producing an Fe(II) ion detection agent, comprising the step of:
mixing a compound represented by formula (I) (fluorescence probe):

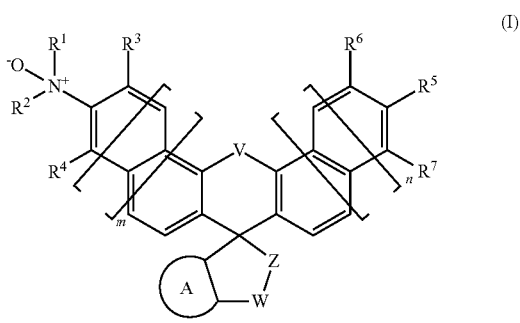

wherein
$R^1$ and $R^2$ are the same or different and represent lower alkyl, carboxy lower alkyl, aryl, or aryl lower alkyl;
$R^3$ and $R^4$ are the same or different and represent hydrogen, halogen, or lower alkyl;
$R^1$ and $R^2$ may be taken together with the nitrogen atom to which they are attached to form a pyrrolidine ring, a piperidine ring, a morpholine ring, or an optionally substituted piperazine ring;
$R^1$ and $R^3$ may be taken together to form trimethylene;
$R^2$ and $R^4$ may be taken together to form trimethylene;
$R^5$ may be hydrogen, optionally protected hydroxyl, lower alkoxy, or a group represented by formula (A): —$NR^{51}R^{52}$ wherein $R^{51}$ and $R^{52}$ are the same or different and represent lower alkyl, carboxy lower alkyl, aryl, or aryl lower alkyl, or $R^{51}$ and $R^{52}$ may be taken together with the nitrogen atom to which they are attached to form a pyrrolidine ring, a piperidine ring, a morpholine ring, or an optionally substituted piperazine ring;
$R^6$ and $R^7$ are the same or different and represent hydrogen, halogen, or lower alkyl;
when $R^5$ is the group represented by formula (A), $R^{51}$ and $R^6$ may be taken together to form trimethylene, or $R^{52}$ and $R^7$ may be taken together to form trimethylene;
ring A represents an optionally substituted aromatic ring or an optionally substituted heteroaromatic ring;
V represents O or $SiR^{10}R^{11}$ wherein $R^{10}$ and $R^{11}$ are the same or different and represent hydrogen or lower alkyl;
W represents $CH_2$, CO, or $S(O)_p$;
Z represents O or $NR^9$ wherein $R^9$ represents hydrogen or alkyl;
m and n are the same or different and represent 0 or 1; and
p represents 1 or 2,
with a compound having at least three coordinating positions.

Advantageous Effects of Invention

The Fe(II) ion detection agent according to the present invention comprises a compound represented by formula (I) (fluorescence probe) and a compound having at least three coordinating positions. The agent can fluorescently detect Fe(II) ions with higher sensitivity, faster than the fluorescence probe alone.

Specifically, the fluorescence probe selectively reacts with Fe(II) ions, and the N-oxide is reduced and changed to amino to thereby emit intense fluorescence. Patent Literature 6 (JP2013-193990A) states that the fluorescence probe has been recognized as being non-responsive to inactive Fe(II) ions that have been stabilized by a chelating agent, such as 2,2'-bipyridyl (e.g., paragraphs [0024] and [0098], and FIG. 7 of Patent Literature 6). However, contrary to expectation, adding a compound having at least three coordinating positions to the 1.5 fluorescence probe has been found to make the probe capable of fluorescently detecting Fe(II) ions faster with higher sensitivity. For example, the time period of one hour required for measurement using the fluorescence probe alone can be significantly shortened to about 5 to 10 minutes (e.g., test example 1, and charts (e) and (f) of FIG. 2).

The Fe(II) ion detection method according to the present invention only mixes an inexpensive and readily available compound having at least three coordinating positions, such as NTA (nitrilotriacetic acid) and ethylenediaminetetraacetic acid (EDTA), with the fluorescence probe, and the method can be performed through a very simple operation. Thus, the method is highly versatile.

The Fe(II) ion detection agent according to the present invention enables selective and quantitative detection of an increase or decrease in Fe(II) ions in a test tube or cells, quickly and highly sensitively with a fluorescence microscope or the like. Thus, the agent is extremely useful in research for elucidating the pathological conditions of diseases with which iron may be associated. The agent is also highly useful in various situations, such as clinical setting and pharmaceutical development, where quick testing is required.

In addition, Fe(II) ions play a role at the initial phase of corrosion occurring in iron as a material. Thus, the agent can also be used in research for ascertaining the corrosion mechanism of iron in marine vessels and the like. More specifically, the Fe(II) ion detection agent according to the present invention can contribute not only to medical science but also to material science.

DESCRIPTION OF EMBODIMENTS

Figure 1:
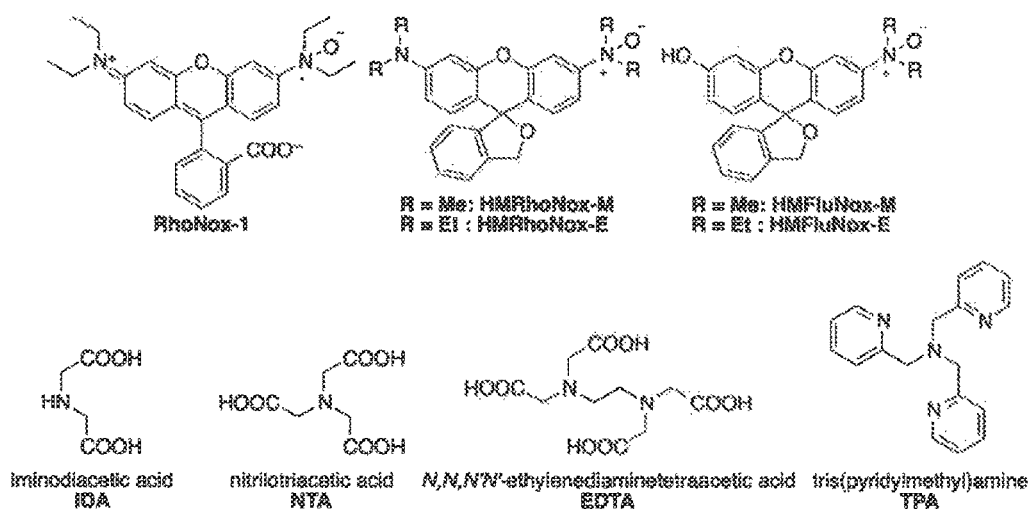
FIG. 1: The upper part shows the structure of N-oxide-containing fluorescence probe molecules for Fe(II) ions, each containing as a fluorophore RhoNox-1, hydroxymethyl rhodamine (HMRhoNox-M, HMRhoNox-E), or hydroxymethyl rhodol (HMFluNox-M, HMFluNox-E). The lower part shows the structure and the name of the polydentate ligand compounds used in this specification.

The following describes the present invention in more detail.
1. Fe(Ie) on Detection Agent of the Present Invention.

The Fe(II) ion detection agent of the present invention comprises a compound represented by formula (I) (fluorescence probe) in combination with a compound having at least three coordinating positions (which may be hereinafter referred to as "polydentate ligand compound").
(i) Compound-Represented by Formula (I) (Fluorescence Probe)

The compound represented by formula (I) contains an N-oxide site, which selectively reacts with an Fe(II) ion to thereby change into amino. Because the resulting amino-containing compound emits intense fluorescence, the compound represented by formula (I) can highly selectively and sensitively detect Fe(II) ions (a fluorescence characteristic). Thus, the compound is useful as an Fe(II) ion selective fluorescence probe.

The Fe(II) ion, which is the target for detection in the present invention, encompasses not only free Fe(II) ions but also compounds containing an Fe(II) ion to which a ligand-like compound (e.g., citric acid, amino acid, and protoporphyrin IX) is coordinated.

Examples of "lower alkyl" represented by $R^1$, $R^2$, $R^3$, $R^4$, $R^{51}$, $R^{52}$, $R^6$, or $R^7$ include linear or branched $C_{1-6}$ alkyl. Specific examples include methyl, ethyl, n-propyl, isopropyl, n-butyl, isobutyl, tert-butyl, sec-butyl, n-pentyl, neopentyl, n-hexyl, isohexyl, and 3-methylpentyl. Preferable examples include $C_{1-3}$ alkyl (i.e., methyl, ethyl, n-propyl, and isopropyl), and more preferable examples include methyl and ethyl.

The "carboxy lower alkyl" represented by $R^1$, $R^2$, $R^{51}$, or $R^{52}$ is a group formed by substituting at least one hydrogen atom of the lower alkyl listed above with carboxyl. Examples include linear or branched $C_{1-6}$ alkyl having 1 to 3 (in particular 1) carboxyl groups. Specific examples include carboxymethyl, 2-carboxyethyl, 3-carboxypropyl, and 4-carboxybutyl, with 2-carboxyethyl being preferable.

Examples of "aryl" represented by $R^1$, $R^2$, $R^{51}$, or $R^{52}$ include monocyclic or bicyclic aryl. Specific examples include phenyl, toluyl, xylyl, and naphthyl, with phenyl being preferable.

The "aryl lower alkyl" represented by $R^1$, $R^2$, $R^{51}$, or $R^{52}$ is a group formed by substituting at least one hydrogen atom of the lower alkyl listed above with aryl. Examples include phenyl-$C_{1-6}$ alkyl, such as benzyl and phenethyl, with benzyl being preferable.

Examples of "halogen" represented by $R^3$, $R^4$, $R^6$, or $R^7$ include fluorine, chlorine, bromine, and iodine.

Examples of "lower alkoxy" represented by $R^5$ include linear or branched $C_{1-6}$ alkoxy. Specific examples include methoxy, ethoxy, n-propyloxy, isopropyloxy, n-butyloxy, isobutyloxy, tert-butyloxy, sec-butyloxy, n-pentyloxy, neopentyloxy, n-hexyloxy, isohexyloxy, and 3-methyl pentyloxy.

Examples of the protecting group in "optionally protected hydroxyl" represented by $R^5$ include methoxymethyl (MOM), 2-tetrahydropyranyl (THP), and acetyl (Ac).

The phrase "$R^1$ and $R^2$ may be taken together with the nitrogen atom to which they are attached to form a pyrrolidine ring, a piperidine ring, a morpholine ring, or an optionally substituted piperazine ring" means that the group represented by the following formula:

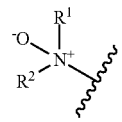

wherein $R^1$ and $R^2$ are as defined above
is preferably the group represented by the following formulae:

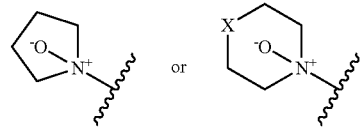

wherein X represents O, $CH_2$, or $NR^{12}$ wherein $R^{12}$ represents hydrogen or alkyl carbonyl.

Examples of "alkyl carbonyl" represented by $R^{12}$ include $C_{2-6}$ alkyl carbonyl. Specific examples include acetyl, propionyl, butyryl, and isobutyryl. Preferable examples include $C_{2-3}$ alkyl carbonyl, such as acetyl and propionyl, and more preferable examples include acetyl.

The phrase "$R^1$ and $R^3$ may be taken together to form trimethylene" (—$CH_2CH_2CH_2$—; the same applies hereinafter) and/or the phrase "R² and R⁴ may be taken together to form trimethylene" means that the group represented by the following formula:

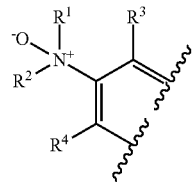

wherein R¹, R², R³, and R⁴ are as defined above
is the group represented by the following formulae;

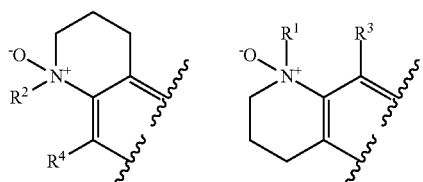

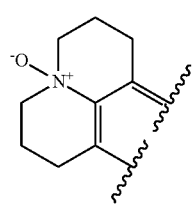

wherein R¹, R², R³, and R⁴ are as defined above.

When $R^5$ is the group represented by formula (A), $R^{51}$ and $R^{52}$ may be taken together with the nitrogen atom to which they are attached to form a pyrrolidine ring, a piperidine ring, or a morpholine ring. This means that the group represented by the following formula:

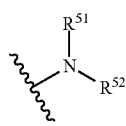

wherein $R^{51}$ and $R^{52}$ are as defined above
is preferably the group represented by the following formulae:

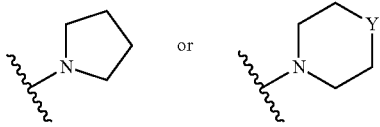

wherein Y represents O, CH₂, or NR¹³ wherein R¹³ represents hydrogen or alkyl carbonyl.

Examples of "alkyl carbonyl" represented by $R^{13}$ include $C_{2-6}$ alkyl carbonyl. Specific examples include acetyl, propionyl, butyryl, and isobutyryl. Preferable examples include $C_{2-3}$ alkyl carbonyl, such as acetyl and propionyl. More preferable examples include acetyl.

When $R^5$ is the group represented by formula (A), $R^{51}$ and $R^6$ may be taken together to form trimethylene, and/or $R^{52}$ and $R^7$ may be taken together to form trimethylene. This means that the group represented by the following formula:

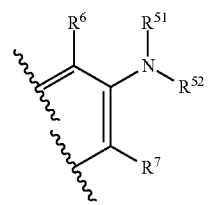

wherein $R^{51}$, $R^{52}$, $R^6$, $R^7$, and n are as defined above
is the group represented by the following formulae:

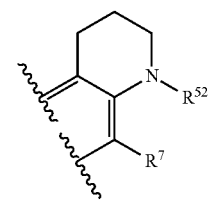 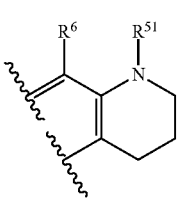

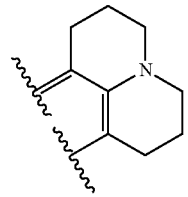

wherein $R^{51}$, $R^{52}$, $R^6$, and $R^7$ are as defined above.

Examples of the aromatic ring in the "optionally substituted aromatic ring" in ring A include monocyclic, bicyclic or tricyclic aromatic rings. Specific examples include benzene ring, naphthalene ring, anthracene ring, and phenanthrene ring. Examples of the substituent for the aromatic ring include optionally protected hydroxyl, lower alkoxy, halogen, carboxyl, lower alkoxycarbonyl, —N═C═O, —N═C═S, sulfo, and active ester. The aromatic ring may have 1 to 3 of these substituents.

Examples of the heteroaromatic ring in the "optionally substituted heteroaromatic ring" in ring A include monocyclic, bicyclic, or tricyclic heteroaromatic rings containing 1 to 3 atoms selected from the group consisting of oxygen, nitrogen, and sulfur. Examples include thiophene ring, furan ring, pyrrole ring, imidazole ring, pyridine ring, pyrazine ring, pyrimidine ring, pyridazine ring, indole ring, quinoline ring, isoquinoline ring, phthalazine ring, naphthyridine ring, quinoxaline ring, quinazoline ring, and acridine ring. Examples of the substituent for the heteroaromatic ring include optionally protected hydroxyl, lower alkoxy, halogen, carboxyl, lower alkoxycarbonyl, —N═C═O, N═C═S, sulfo, and active ester. The heteroaromatic ring may have 1 to 3 of these substituents.

Ring A is preferably represented by formula (a):

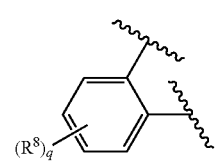

(a)

wherein $R^8$ represents optionally protected hydroxyl, lower alkoxy, halogen, carboxyl, lower alkoxycarbonyl, —N═C═O, —N═C═S, sulfo, and active ester; q represents 0, 1, 2 or 3; and when q is 2 or 3, the two or three $R^8$ may be the same or different.

Examples of the protecting group in the "optionally protected hydroxyl" that is a substituent attached to ring A (including $R^8$) include methoxymethyl (MOM), 2-tetrahydropyranyl (THP), and acetyl (Ac).

Examples of the "lower alkoxy" that is a substituent attached to ring A (including $R^8$) include linear or branched $C_{1-6}$ (in particular $C_{1-3}$) alkoxy. Specific examples include methoxy, ethoxy, n-propyloxy, and isopropyloxy.

Examples of the "halogen" that is a substituent attached to ring A (including $R^8$) include fluorine, chlorine, bromine, and iodine.

Examples of the "lower alkoxycarbonyl" that is a substituent attached to ring A (including $R^8$) include linear or branched ($C_{1-6}$ alkoxy) carbonyl, such as methoxycarbonyl, ethoxycarbonyl, n-propyl oxycarbonyl, isopropyl oxycarbonyl, and tert-butyl oxycarbonyl.

The active ester that is a substituent attached to ring A (including $R^8$) is a group in which carboxyl (—COOH) has been replaced with a highly reactive active ester. Examples include active ester obtained using N-hydroxy succinimide (e.g., —C(═O)OSu: Su is a succinimide group), a group formed by converting carboxylic acid into mixed acid anhydride (e.g., —C(═O)OC(═O)R: R is $C_{1-6}$ alkyl), and an imidazolide group obtained using CDI (e.g., —C(═O)—Im: Im is 1-imidazolyl).

In formula (a), q is preferably 0, 1, or 2, more preferably 0 or 1, and particularly more preferably 0. When q is 1, the binding site to which $R^8$ binds in the benzene ring is preferably as shown below,

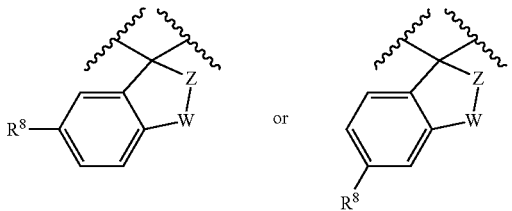

wherein $R^8$, W, and Z are as defined above.

W is $CH_2$, CO, or $S(O)_p$, preferably $CH_2$ or CO, and more preferably CO.

Z is O or $NR^9$ wherein $R^9$ is hydrogen or alkyl, and Z is preferably O.

Examples of alkyl represented by $R^9$ include linear or branched $C_{1-6}$ alkyl, and specific examples include methyl, ethyl, n-propyl, and isopropyl.

m is 0 or 1, and is preferably 0.
n is 0 or 1, and is preferably 0.
p is 1 or 2, and is preferably 2.

Preferable examples of the compound represented by formula (I) include compounds wherein $R^1$ and $R^2$ are the same or different and represent $C_{1-6}$ alkyl; $R^1$ and $R^2$ may be taken together with the nitrogen atom to which they are attached to form a morpholine ring, or an optionally substituted piperazine ring (preferably an optionally substituted piperazine ring, and more preferably a piperazine ring substituted with alkyl carbonyl); $R^3$ and $R^4$ are hydrogen, or $R^1$ and $R^3$ may be taken together to form trimethylene; $R^2$ and $R^4$ may be taken together to form trimethylene; $R^5$ may be optionally protected hydroxyl or a group represented by formula (A): —$NR^{51}R^{52}$; when $R^5$ is the group represented by formula (A), $R^{51}$ and $R^{52}$ are the same or different and represent $C_{1-6}$ alkyl; $R^6$ and $R^7$ represent hydrogen, or $R^{52}$ and $R^6$ may be taken together to form trimethylene; $R^{52}$ and $R^7$ may be taken together to form trimethylene; q is 0; W is $CH_2$ or CO; Z is O; m is 0; and n is 0.

More preferable examples of the compound represented by formula (I) include compounds wherein $R^1$ and $R^2$ are the same or different and represent $C_{1-6}$ alkyl; $R^3$ and $R^4$ are hydrogen or $R^1$ and $R^3$ may be taken together to form trimethylene; $R^2$ and $R^4$ may be taken together to form trimethylene; $R^5$ may be optionally protected hydroxyl or a group represented by formula (A): —$NR^{51}R^{52}$; when $R^5$ is the group represented by formula (A), $R^{51}$ and $R^{52}$ are the same or different and represent $C_{1-6}$ alkyl; $R^6$ and $R^7$ represent hydrogen, or $R^{51}$ and $R^6$ may be taken together to form trimethylene; $R^{52}$ and $R^7$ may be taken together to form trimethylene; q is 0; W is $CH_2$ or CO; Z is O; m is 0; and n is 0.

Still more preferable examples of the compound in the present invention include compounds represented by formula (I) wherein $R^1$ and $R^2$ are the same or different and represent $C_{1-3}$ alkyl; $R^3$ and $R^4$ are hydrogen; $R^5$ may be optionally protected hydroxyl or a group represented by formula (A): —$NR^{51}R^{52}$; when $R^5$ is the group represented by formula (A), $R^{51}$ and $R^{52}$ are the same or different and represent $C_{1-3}$ alkyl; $R^6$ and $R^7$ are hydrogen; $R^8$ is hydrogen; q is 0; W is $CH_2$ or CO; Z is O; m is 0; and n is 0.

Particularly more preferable examples of the compound in the present invention include compounds represented by formula (IA):

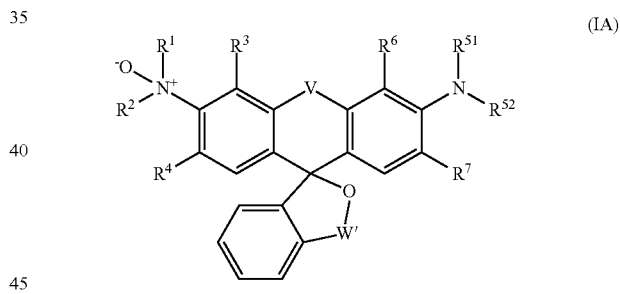

wherein W' represents $CH_2$ or CO; and $R^1$, $R^2$, $R^3$, $R^4$, $R^{51}$, $R^{52}$, $R^6$, $R^7$, and V are as defined above.

V is O or $SiR^{10}R^{11}$, and is preferably O. $R^{10}$ and $R^{11}$ are the same or different and represent hydrogen or lower alkyl, with lower alkyl being preferable. Examples of lower alkyl for $R^{10}$ or $R^{11}$ include linear or branched $C_{1-4}$ alkyl, and preferably $C_{1-2}$ alkyl. Specific examples include methyl, ethyl, n-propyl, and isopropyl.

Of these, particularly preferable compounds are those wherein V is O; $R^1$, $R^2$, $R^{51}$, and $R^{52}$ are the same or different and represent $C_{1-3}$ alkyl (more preferably methyl or ethyl, particularly more preferably ethyl); and $R^3$, $R^2$, $R^6$, and $R^7$ are hydrogen.

In the compound represented by formula (I), when group $R^5$ contains an electron-donating atom, such as nitrogen and oxygen, (e.g., —$NR^{51}R^{52}$ and hydroxyl), the double bonds of the conjugated system of the benzene ring in the xanthene frame structure may shift because of the electron donation effect, thereby forming a compound with an opened ring. For example, when group $R^5$ is —$NR^{51}R^{52}$, the ring opens, thereby giving a compound represented by formula (Ia):

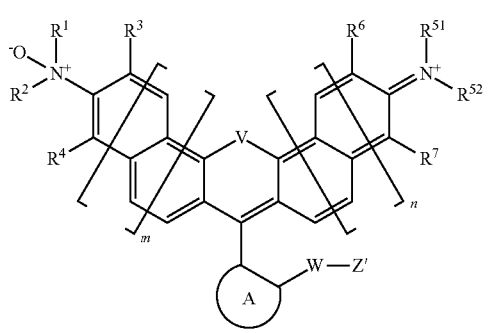

(1a)

wherein $R^1$, $R^2$, $R^3$, $R^4$, $R^5$, $R^6$, $R^7$, $R^8$, V, W, Z, ring A, m, and n are as defined above. As another example, when group $R^5$ is hydroxyl, the ring opens, thereby giving a compound represented by formula (Ib):

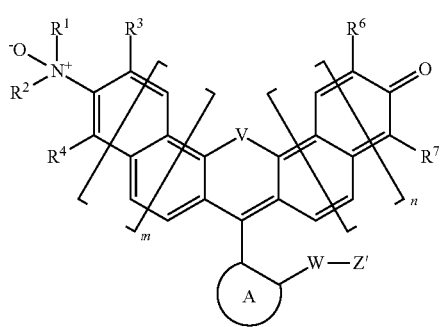

(1b)

wherein $R^1$, $R^2$, $R^3$, $R^4$, $R^5$, $R^6$, $R^7$, $R^8$, V, W, Z, ring A, m, and n are as defined above.

When the compound represented by formula (I) and/or the compound represented by formula (Ia) are dissolved in a medium (solvent), the compound represented by formula (I) and the compound represented by formula (Ia) typically stay in equilibrium. The point at which the equilibrium settles can vary depending on the polarity, pH, or other factors of the medium (solvent). Thus, in this specification, the compound represented by formula (I) and the compound represented by formula (Ia) are collectively referred to as a "compound represented by formula (I)."

The compound represented by formula (I) can be produced, for example, as described below

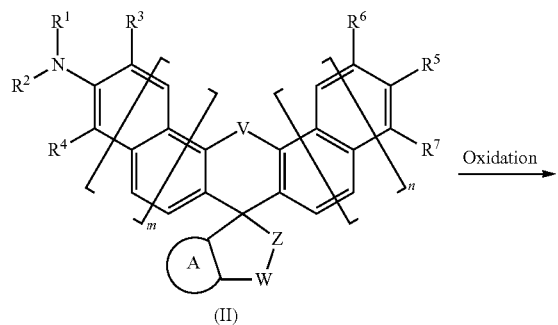

(II)

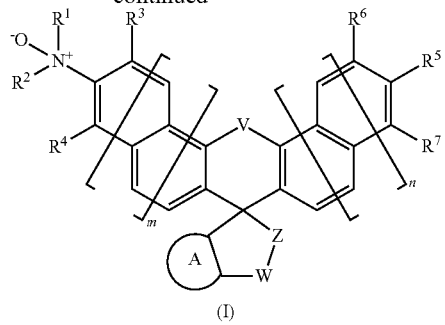

(I)

wherein $R^1$, $R^2$, $R^3$, $R^4$, $R^5$, $R^6$, $R^7$, $R^8$, V, W, Z, ring A, m, and n are as defined above.

The compound represented by formula (II) can be readily available, or produced by or with reference to a known method.

Of the compound represented by formula (II), compounds wherein W is C=O are commercially available, or can be produced by or with reference to, for example, the procedure disclosed in Bioorg. Med. Chem. 17 (2009) 6952-6958, Org. Lett. 12 (2007) 496-499, Org. Lett. 13 (2010), 6354-6357, Tetrahedron 61 (2005) 3097-3105.

Of the compound represented by formula (II), compounds wherein W is $CH_2$ can be produced by or with reference to, for example, the procedure disclosed in Organic Letters 2010, 12, 3219-21, J. Am. Chem. Soc. 2011, 133, 12960-3.

The compound represented by formula (I) can be produced by subjecting the compound represented by formula (II) to oxidation (a reaction for oxidizing the nitrogen atom). For example, the compound represented by formula (I) can be produced by or with reference to the procedure disclosed in Patent Literature 6.

The compound represented by formula (II), which is a starting material, may transform into a compound represented by formula (IIa):

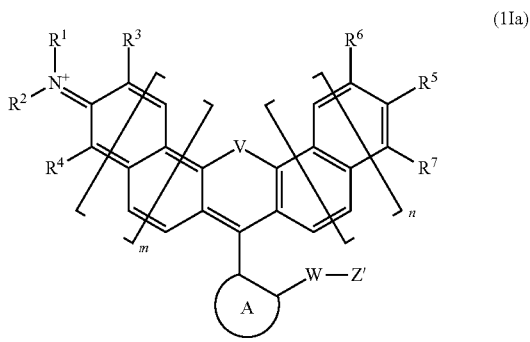

(IIa)

wherein $R^1$, $R^2$, $R^3$, $R^4$, $R^5$, $R^6$, $R^7$, $R^8$, V, W, Z, ring A, m, and n are as defined above, because the double bonds of the conjugated system of the benzene ring in the xanthene frame structure shift due to the electron donation effect of the nitrogen atom to which $R^1$ and $R^2$ are attached, thereby opening the ring.

This compound typically emits intense fluorescence. When the compound represented by formula (II) and/or the compound represented by formula (IIa) is dissolved in a medium (solvent), the compound represented by formula (II) and the compound represented by formula (IIa) typically stay in equilibrium. The point at which the equilibrium settles can vary depending on the polarity, pH, or other factors of the medium (solvent). Thus, in this specification, the compound represented by formula (II) and the compound represented by formula (IIa) are collectively referred to as a "compound represented by formula (II)."

(ii) Compound Having at Least Three Coordinating Positions

Examples of the compound having at least three coordinating positions (polydentate ligand compound) include compounds having the same or different at least three coordinating positions selected from the group consisting of amino, hydroxyl, ether (—O—), carboxyl, phosphonic acid group, and nitrogen-containing heteroaromatic ring.

As used herein, the "amino" refers to a moiety containing a nitrogen atom with $sp^3$ hybridized orbitals.

The "nitrogen-containing heteroaromatic ring" refers to a moiety of a heteroaromatic ring having 1 to 3 nitrogen atoms attached to it (e.g., pyridine ring, imidazole ring, and pyrrole ring). The nitrogen-containing heteroaromatic ring may optionally have 1 to 3 substituents (e.g., aryl, such as phenyl, toluyl, xylyl, and mesityl; and alkyl, such as methyl and ethyl).

Of the coordinating positions, amino, carboxyl, phosphonic acid group, and nitrogen-containing heteroaromatic ring (e.g., pyridine ring and pyrrole ring) are preferable. Amino, carboxyl, and pyridine ring are more preferable. Amino and pyridine ring are still more preferable. The number of coordinating positions in the compound is typically 3 to 16, preferably 4 to 12, more preferably 4 to 10, and still more preferably 4 to 5.

When the compound having at least three coordinating positions contains a nitrogen atom, the number of coordinating positions is preferably within 5.

When the compound having at least three coordinating positions contains a pyridine ring, the number of coordinating positions is preferably within 3.

It appears that such a compound having at least three coordinating positions quickly forms a complex with an Fe(II) ion, and the complex reacts with the compound represented by formula (I) (fluorescence probe), thereby facilitating a reduction reaction (deoxygenation) of the N-oxide. Given this reaction mechanism, when the compound having at least three coordinating positions forms a complex with an Fe(II) ion, the compound preferably forms a vacant coordination site with which a fluorescence probe can react.

Specific examples of compounds having at least three coordinating positions include aminocarboxylic acid compounds, such as iminodiacetic acid (IDA), nitrilotriacetic acid (NTA), N,N,N',N'-ethylenediaminetetraacetic acid (EDTA), 1,3-propanediamine tetraacetic acid (PDTA), diethylenetriamine pentaacetic acid (DTPA), hydroxyethyl ethylenediamine triacetic acid (HEDTA), triethylenetetraaminehexaacetic acid (TTHA), 1,2-diaminocyclohexane tetraacetic acid (CyDTA), glycol ether diamine tetraacetic acid (GEDTA or EGTA), N,N-bis(2-hydroxybenzyl)ethylenediamine diacetic acid (HBED), ethylenediamine dipropionic acid (EDDP), ethylenediamine diacetic acid (EDDA), ethylenediamine disuccinic acid (EDDS), 1,3-diamino-2-hydroxypropane tetraacetic acid (DPTA-OH), dihydroxyethyl glycine (DHEG), hexamethylenediamine tetraacetic acid (HDTA), hydroxyethyl iminodiacetic acid (HIDA), diaminopropane tetraacetic acid(Methyl-EDTA), nitrilotripropionic acid (NTP), L-glutamic acid diacetic acid (GLDA), O,O'-bis-2-aminophenyl-N,N,N',N'-tetraacetic acid (BAPTA), and o-aminophenol-N,N,O-triacetic acid (APTRA); phosphonic acid compounds, such as ethylenediamine tetrakis(methylene phosphonic acid) (EDTPO), nitrilotris(methylene phosphonic acid) (NTPO), hydroxyethylidene diphosphonic acid (HEDP), and phosphonobutane tricarboxylic acid (PBTC); pyridylmethyl amine compounds, such as tris(2-pyridylmethyl)amine (TPA), and dipicolylamine (DPA); cyclic polyamine compounds, such as 1,4,7-triazacyclononane (TACN), 1,4,7,10-tetra-azacyclo-dodecane (CYCLEN), and 1,4,8,11-tetra-azacyclo-tetradecane (CYCLAM); porphyrin, and its derivatives; protoporphyrin IX, and its derivatives; phthalocyanine, and its derivatives; cyclic polypyrrole derivatives; and salts of these compounds. Of these, preferable examples include pyridylmethyl amine compounds and aminocarboxylic acid compounds, and more preferable examples include pyridylmethyl amine compounds.

Examples of the salts of compounds having at least three coordinating positions include alkali metal salts (e.g., lithium salt, sodium salt, and potassium salt), alkaline-earth metal salts (e.g., calcium salt), ammonium salts, and tetraalkyl ammonium salts. In particular, when the compound contains carboxylic acid, alkali metal salts (sodium salt) are preferable.

(iii) Fe(II) Ion Detection Agent

The Fe(II) ion detection agent according to the present invention comprises a compound represented by formula (I) (fluorescence probe) in combination with a compound having at least three coordinating positions (polydentate ligand compound).

The Fe(II) ion detection agent according to the present invention is not particularly limited as long as the agent comprises the two components, and the agent can be in various forms. Examples include agents in the form of a mixture of the compound represented by formula (I) (fluorescence probe) with a compound having at least three coordinating positions (polydentate ligand compound) (e.g., compositions, and combination agents), and agents in the form of separate components each contained in individual containers (e.g., kit). Agents in the form of a mixture also include agents in solids form (e.g., powder and crystal) as well as agents in the form of solution or dispersion obtained by dissolving or dispersing the components in a medium (e.g., water and a buffer solution). Agents in the form of separate components each contained in individual containers may also be in the form of individual solids, or individual solutions or dispersions obtained by dissolving or dispersing the components in a medium (e.g., water and a buffer solution).

2. Method for Detecting Fe(II) Ion

The method for measuring (or detecting) Fe(II) ions according to the present invention comprises the steps of (1) mixing a specimen containing Fe(II) ions with the Fe(II) ion detection agent according to the present invention, and (2) measuring a fluorescence spectrum of the obtained mixture. Specifically, Fe(II) ions can be measured by mixing a specimen containing Fe(II) ions with the Fe(II) ion detection agent of the present invention in a suitable buffer solution, incubating the mixture, and irradiating the incubated mixture with excitation light to measure the fluorescence.

The buffer solution for use is not particularly limited, and examples include known buffer solutions, such as HEPES buffer solution (pH of 7.4).

The concentration of the compound represented by formula (I) (fluorescence probe) in a buffer solution is not particularly limited, and is typically about 0.1 µM to 1 mM, preferably about 1 µM to 0.1 mM, and more preferably about 5 µM to 20 µM. The concentration of the compound having at least three coordinating positions (polydentate ligand compound) in a buffer solution is also not particularly limited, and is typically about 0.1 μM to 10 mM, preferably about 1 μM to 1 mM, and more preferably about 10 μM to 500 μM.

In a buffer solution, the compound having at least three coordinating positions (polydentate ligand compound) is present in an amount of typically about 1 to 1,000 moles, and preferably about 10 to 100 moles, per mole of the compound represented by formula (I) (fluorescence probe).

The temperature and the time period for incubation are not particularly limited. For example, the incubation can be performed at about 0 to 40° C. for about 10 minutes to 2 hours. When cells or tissues serve as a specimen, the temperature suitable for the culturing is preferably applied (e.g., 37° C. for human-derived cells or tissues).

The fluorescence can be measured by using a commercially available fluorometer. The dynamics of Fe(II) ions in cells can be investigated by observation using a known technique, such as a fluorescence microscope and a confocal laser scanning fluorescence microscope.

The use of the method according to the present invention enables more highly sensitive and faster fluorescence detection of Fe(II) ions, as compared with the use of the fluorescence probe disclosed in Patent Literature 6.

Examples

The following Examples describe the present invention in detail. However, the present invention is not limited to the Examples.

The following Examples used silica gel column chromatography or alumina chromatography to purify compounds, and thin-layer chromatography (TLC), ESI-MS (JEOL JMS-T100TD), $^1$H-NMR, or $^{13}$C-NMR (JEOL ECA-500 spectrometer) to identify compounds.

Example 1

3'-(Diethylamino)-N,N-diethyl-3-oxo-3H-spiro[isobenzofuran-1,9'-xanthene]-6'-amine oxide (which is hereinafter referred to as "RhoNox-1") was synthesized in accordance with the procedure disclosed in Patent Literature 6.

Example 2

(1) 3'-(Dimethylamino)-N,N-dimethyl-3H-spiro[isobenzofuran-1,9'-xanthene]-6'-amine oxide (which is hereinafter referred to as "HMRhoNox-M" or "RhoNox-2") was synthesized as described below.

$N^{3'},N^{3'},N^{6'},N^{6'}$-tetramethyl-3H-spiro[isobenzofuran-1,9'-xanthene]-3',6'-diamine, which is a precursor compound, was synthesized in accordance with a procedure disclosed in, for example, Organic Letters 2010, 12, 3219-21, J. Am. Chem. Soc. 2011, 133, 12960-3. 90 mg (0.24 mmol) of $N^{3'},N^{3'},N^{6'},N^{6'}$-tetramethyl-3H-spiro[isobenzofuran-1,9'-xanthene]-3',6'-diamine was dissolved in 18 mL of ethyl acetate and cooled to 0° C. with stirring. 83 mg (0.48 mmol) of meta-chloroperbenzoic acid was gradually added thereto, and the mixture was allowed to return to room temperature, followed by stirring for 1 hour. The solvent was distilled off under reduced pressure, and the obtained residue was purified by alumina column chromatography (chloroform:methanol=50:1 to 20:1) to thereby obtain HMRhoNox-M as a colorless powder (64 mg, yield 71%).

$^1$H NMR (400 MHz, CDCl$_3$) δ: 7.91 (d, J=2.3 Hz, 1H), 7.44 (dd, J=8.6 Hz, 2.3 Hz, 1H), 7.37 (m, 2H), 7.26 (m, 1H), 7.04 (d, J=8.6 Hz, 1H), 6.90 (d, J=7.4 Hz, 1H), 6.80 (d, J=6.9 Hz, 1H), 6.46 (m, 2H), 5.30 (dd, J=20.0 Hz, 12.6 Hz, 2H), 3.58 (d, J=4.0 Hz, 6H), 2.97 (s, 6H).

$^{13}$C NMR (MHz, CDCl$_3$) δ: 154.5, 151.5, 151.3, 150.9, 144.5, 139.1, 129.9, 129.2, 128.4, 128.2, 128.2, 125.7, 123.8, 120.7, 114.2, 111.7, 109.2, 109.0, 98.5, 83.3, 72.1, 63.2, 63.1, 40.3.

HRMS (ESI+): m/z calculated for $C_{24}H_{25}N_2O_3^+$: 389.1860. found 389.1871.

(2) 3'-(Diethylamino)-N,N-diethyl-3H-spiro[isobenzofuran-1,9'-xanthene]-6'-amine oxide (which is hereinafter referred to as "RhoNox-E") was synthesized as described below.

$N^{3'},N^{3'},N^{6'},N^{6'}$-tetraethyl-3H-spiro[isobenzofuran-1,9'-xanthene]-3',6'-diamine, which is a precursor compound, was synthesized in accordance with a procedure disclosed in, for example, Organic Letters 2010, 12, 3219-21, J. Am. Chem. Soc. 2011, 133, 12960-3. 267 mg (0.62 mmol) of $N^{3'},N^{3'},N^{6'},N^{6'}$-tetraethyl-3H-spiro[isobenzofuran-1,9'-xanthene]-3',6'-diamine was dissolved in 20 mL of ethyl acetate and cooled to 0° C. with stirring. 214 mg (1.24 mmol) of meta-chloroperbenzoic acid was gradually added thereto, and the mixture was allowed to return to room temperature, followed by stirring for 1 hour. The solvent was distilled off under reduced pressure, and the obtained residue was purified by alumina column chromatography (chloroform:methanol=20:1 to 10:1) to thereby obtain HMRhoNox-E as a pale purple powder (245 mg, yield 53%).

$^1$H NMR (500 MHz, CDCl$_3$) δ: 7.78 (d, J=1.9 Hz, 1H), 7.37 (m, 2H), 7.28 (m, 2H), 7.03 (d, J=8.7 Hz, 1H), 6.92 (d, J=7.7 Hz, 1H), 6.77 (d, J=8.7 Hz, 1H), 6.42 (m, 4H), 5.29 (dd, J=16.4 Hz, 12.6 Hz, 2H), 3.70 (m, 4H), 3.35 (q, J=7.1 Hz, 4H), 1.16 (q, J=6.6 Hz, 12H).

$^{13}$C NMR (1.25 MHz, CDCl$_3$) δ: 151.7, 151.0, 149.0, 148.8, 144.4, 139.2, 129.6, 129.4, 128.3, 128.1, 125.5, 123.8, 120.6, 115.5, 111.1, 110.7, 108.5, 97.5, 83.3, 71.9, 66.9, 44.4, 12.5, 8.3.

HRMS (ESI+): m/z calculated for $C_{23}H_{33}N_2O_3^+$: 445.2486. found 445.2501.

(3) 3'-Hydroxy-N,N-dimethyl-3H-spiro[isobenzofuran-1,9'-xanthene]-6'-amine oxide (which is hereinafter referred to as "HMFluNox-M") was synthesized as described below.

3'-(Dimethylamino)-3H-spiro[isobenzofuran-1,9'-xanthene]-6'-ol, which is a precursor compound, was synthesized in accordance with a procedure disclosed in, for example, Organic Letters 2010, 12, 3219-21, J. Am. Chem. Soc. 2011, 133, 12960-3. 34 mg (0.098 mmol) of 3'-(dimethylamino)-3H-spizo[isobenzofuran-1,9'-xanthene]-6'-ol was dissolved in 4 mL of ethyl acetate and cooled to 0° C. with stirring. 34 mg (0.20 mmol) of meta-chloroperbenzoic acid was gradually added thereto, and the mixture was allowed to return to room temperature, followed by stirring for 1 hour. The solvent was distilled off under reduced pressure, and the obtained residue was purified by alumina column chromatography (chloroform:methanol=10:1 to 8:1) to thereby obtain HMFluNox-M as a colorless powder (21 mg, yield 58%).

$^1$H NMR (400 MHz, CDCl$_3$) δ: 8.47 (s, 1H), 7.28 (s, 2H), 7.18-7.17 (m, 1H), 7.11 (d, J=2.8 Hz, 1H), 6.93 (s, 2H), 6.83 (d, J=8.0 Hz, 1H), 6.67 (d, J=8.8 Hz, 1H), 6.48 (dd, J=8.8 Hz, 2.4 Hz, 1H) 5.24, (m, 2H), 3.52 (s, 6H).

$^{13}$C NMR (400 MHz, CDCl$_3$) δ: 159.8, 153.7, 151.5, 151.0, 144.4, 139.0, 129.9, 129.4, 128.4, 128.2, 126.1, 124.0, 120.6, 113.7, 113.4, 112.8, 110.5, 103.1, 83.3, 72.1, 63.1, 62.2.

HRMS (ESI+): m/z calculated for $C_{22}H_{20}NO_4^+$: 362.1387. found 362.1389.

(4) 3'-Hydroxy-N,N-diethyl-3H-spiro[isobenzofuran-1,9'-xanthene]-6'-amine oxide (which is hereinafter referred to as "HMFluNox-E") was synthesized as described below.

3'-(Diethylamino)-3H-spiro[isobenzofuran-1,9'-xanthene]-6'-ol, which is a precursor compound, was synthesized in accordance with a procedure disclosed in, for example, Organic Letters 2010, 12, 3219-21, J. Am. Chem. Soc. 2011, 133, 12960-3. 100 mg (0.27 mmol) of 3'-(diethylamino)-3H-spiro[isobenzofuran-1,9'-xanthene]-6'-ol was dissolved in 10 mL of ethyl acetate and cooled to 0° C. with stirring. 93 mg (0.54 mmol) of meta-chloroperbenzoic acid was gradually added thereto, and the mixture was allowed to return to room temperature, followed by stirring for 1 hour. The solvent was distilled off under reduced pressure, and the obtained residue was purified by alumina column chromatography (chloroform:methanol=20:1 to 10:1) to thereby obtain HMFluNox-E as a colorless powder (102 mg, yield 97%).

$^1$H NMR (400 MHz, CDCl$_3$) δ: 7.72 (d, J=2.4 Hz, 1H), 7.33 (m, 3H), 7.19 (t, J=7.5 Hz, 1H), 7.02 (d, J=9.2 Hz, 1H), 6.72 (d, J=8.7 Hz, 2H), 6.55 (d, J=2.4 Hz, 1H), 6.46 (dd, J=8.7 Hz, 2.4 Hz, 1H), 5.24 (s, 1H), 3.76 (m, 2H), 3.56 (m, 1H), 1.01 (m, 6H).

$^{13}$C NMR (100 MHz, CDCl$_3$) δ: 158.8, 151.1, 150.1, 148.3, 144.6, 138.7, 130.0, 129.8, 128.3, 126.0, 123.2, 120.8, 115.8, 115.2, 112.2, 11.0.8, 101.7, 83.3, 72.2, 66.4, 29.3, 22.2, 13.0, 7.22.

HRMS (ESI+): m/z calculated for $C_{24}H_{24}NO_4^+$: 390.1700. found 390.1695.

(5) 4-(3'-Hydroxy-3-oxo-3H-spiro[isobenzofuran-1,9'-xanthene]-6'-yl)morpholin-4-oxide (which is hereinafter referred to as "FluNox-1") was synthesized as described below.

3'-Hydroxy-6'-morpholino-3H-spiro[isobenzofuran-1,9'-xanthene]-3-one, which is a precursor compound, was synthesized in accordance with a procedure disclosed in, for example, Organic Letters, 2011, 13, 6354-6357. 100 mg (0.23 mmol) of 3'-hydroxy-6'-morpholino-3H-spiro[isobenzofuran-1,9'-xanthene]-3-one was dissolved in 10 mL of dimethyl formamide, and the mixture was stirred at 0° C. for 10 minutes. 47 mg (0.27 mmol) of meta-chloroperbenzoic acid was gradually added thereto, and the mixture was allowed to return to room temperature, followed by stirring for 3 hours. 47 mg (0.27 mmol) of meta-chloroperbenzoic acid was further gradually added thereto. The mixture was stirred for 3 hours, and then the solvent was distilled off under reduced pressure. The obtained residue was purified by silica gel column chromatography (chloroform:methanol=7:1) to thereby obtain FluNox-1 (37 mg, yield 63%).

$^1$H NMR (CD$_3$OD, 500 MHz) δ:8.10 (d, 1H, J=2.3 Hz), 8.05 (d, 1H, J=7.4 Hz), 7.80-7.71 (m, 2H), 7.67 (dd, 1H, J=9.2, 2.3 Hz), 7.22 Cd, 1H, J=7.4 Hz), 7.00 (d, 1H, J=9.2 Hz), 6.65-6.58 (m, 2H), 4.47 (t, 2H, J=11.2 Hz), 4.18-1.12 (m, 2H), 3.94 (d, 2H, J=12.6 Hz), 3.23 (m, 2H).

$^{13}$C NMR (CD$_3$OD, 125 MHz) δ:169.7, 160.1, 155.2, 115.3, 113.0, 109.9, 109.2, 102.4, 82.4, 66.9, 61.6.

HRMS (ESI+): m/z calculated for $C_{24}H_{20}NO_6^+$: 418.1285. found: 418.1304.

(6) 4-Acetyl-1-(3'-hydroxy-3-oxo-3H-spiro[(isobenzofuran-1,9'-xanthene]-6'-yl)-piperazin-1-oxide (which is hereinafter referred to as "FluNox-2") was synthesized as described below.

3'-Hydroxy-6'-(piperazine-1-yl)-3H-spiro[isobenzofuran-1,9'-xanthene]-3-one, which is a precursor compound, was synthesized in accordance with a procedure disclosed in, for example, Chemical Communications, 2013, 49, 10474-10476. 78 mg (0.16 mmol) of 3'-hydroxy-6'-(piperazine-1-yl)-3H-spiro[isobenzofuran-1,9'-xanthene]-3-one was dissolved in 2 mL of pyridine, and 148 μL (1.6 mmol) of acetic anhydride was gradually added thereto at 0° C. The mixture was allowed to return to room temperature, and stirred for 1 hour. The solvent was distilled off under reduced pressure, and the obtained residue was purified by silica gel column chromatography (chloroform:methanol=100:0 to 100:1) to thereby obtain 3'-(4-acetylpiperazine-1-yl)-3-oxo-3H-spiro[isobenzofuran-1,9'-xanthene]-6'-yl-acetate as a pale yellow powder (68 mg, yield 91%).

$^1$H NMR (CDCl$_3$, 500 MHz) δ: 8.02 (dd, J=7.6 Hz, 1H), 7.64 (t, J=7.5 Hz, 1H), 7.62 (t, J=7.5 Hz, 1H), 7.17 (d, J=7.6 Hz, 1H), 7.06 (d, J=2.0 Hz, 1H), 6.81-6.76 (m, 2H), 6.69 (d, J=2.2 Hz, 1H), 6.65 (d, J=8.9 Hz, 1H), 6.60 (dd, J=8.9 Hz, 2.2 Hz, 1H), 3.75-3.72 (m, 2H), 3.60-3.58 (m, 2H), 3.25-3.20 (m, 4H), 2.32 (s, 3H), 2.12 (s, 3H).

$^{13}$C NMR (CD$_3$OD, 125 MHz) δ:169.2, 168.9, 168.8, 152.7, 152.4, 152.0, 151.8, 151.7, 135.0, 129.7, 129.0, 128.7, 126.4, 124.9, 123.9, 117.2, 116.6, 112.2, 110.1, 109.2, 102.2, 82.5, 48.1, 47.9, 45.6, 40.8, 21.2, 21.0.

HRMS (ESI+): m/z calculated for $C_{28}H_{24}N_2O_6Na^+$: 507.1527. found 507.1554.

Subsequently, 90 mg (0.19 mmol) of the obtained 3'-(4-acetylpiperazine-1-yl)-3-oxo-3H-spiro[isobenzofuran-1,9'-xanthene]-6'-yl-acetate was dissolved in 5 mL of dichloromethane, and 48 mg (0.28 mmol) of meta-chloroperbenzoic acid was gradually added thereto at 0° C. The mixture was allowed to return to room temperature and stirred for 5 hours, followed by distillation of the solvent under reduced pressure. The obtained residue was purified by silica gel column chromatography (chloroform:methanol=10:1) to thereby obtain 1-(3'-acetoxy-3-oxo-3H-spiro[isobenzofuran-1,9'-xanthene]-6'-yl)-4-acetylpiperidin-oxide as a colorless powder (26 mg, yield 28%).

$^1$H NMR (CDCl$_3$, 500 MHz) δ: 8.25 (d, J=2.0 Hz, 1H), 8.06 (d, J=7.6 Hz, 1H), 7.72-7.66 (m, 2H), 7.61 (dd, J=8.7 Hz, 2.0 Hz, 1H), 7.18 (t, J=Hz, 1H), 7.14 (d, J=3.1 Hz, 1H), 6.96 (t, J=8.7 Hz, 1H), 6.85 (s, 2H), 4.67 (d, J=13.7 Hz, 2H), 4.43 (t, J=12.5 Hz, 2H), 3.86-3.73 (m, 4H), 3.21 (t, J=10.6 Hz, 4H), 2.33 (s, 3H), 2.18 (s, 3H).

HRMS (ESI+): m/z calculated for $C_{28}H_{24}N_2O_7Na^+$: 523.1476. found 523.1483.

Subsequently, 18 mg (0.036 mmol) of the obtained colorless powder was dissolved in 1.5 mL of methanol, and 0.5 mL of an aqueous solution of 15 mg (0.11 mmol) of potassium carbonate was added thereto, followed by stirring at room temperature for 30 minutes. 1 M Hclaq was then added to neutralize the mixture. The obtained neutralized mixture was extracted with dichloromethane (5 mL×5). The organic layer was dried over magnesium sulfate, and the solvent was distilled off under reduced pressure. The obtained residue was purified by silica gel column chromatography (chloroform:methanol=10:1 to 7:1) to thereby obtain FluNox-2 as a colorless powder (14 mg, yield 82%).

$^3$H NMR (CD$_3$OD, 500 MHz) δ: 8.11 (dd, J=5.2 Hz, 2.3 Hz, 1H), 8.03 (d, J=7.5 Hz, 1H), 7.78 (t, J=7.5 Hz, 1H), 7.73 (t, J=7.4 Hz, 1H), 7.66-7.63 (m, 1H), 7.20 (d, J=7.5 Hz, 1H), 6.99 (d, J=8.6 Hz, 1H), 6.73 (d, J=2.3 Hz, 1H), 6.64 (d, J=9.2 Hz, 1H), 6.58 (d, J=8.6 Hz, 2.3 Hz, 1H), 4.61 (d, J=13.8 Hz, 1H), 4.12-4.10 (m, 2H), 4.00-3.98 (m, 2H), 3.64-3.59 (m, 1H), 3.27-3.26 (m, 21H), 2.16 (s, 3H).

$^{13}$C NMR (CD$_3$OD, 125 MHz) δ:170.5, 169.6, 160.2, 155.3, 152.8, 152.1, 151.7, 135.6, 130.2, 129.3, 128.9, 126.2, 124.8, 123.8, 120.8, 115.4, 112.9, 109.9, 109.2, 102.3, 66.6, 41.1, 36.3, 19.7.

HRMS (ESI+): m/z calculated for $C_{26}H_{23}N_2O_6^+$: 459.1551. found 459.1553.

(7) 4-Acetyl-1-(3'-(4-acetylpiperazine-1-yl)-3-oxo-3H-spiro[isobenzofuran-1,9'-xanthene]-6'-yl) piperazin-1-oxide (which is hereinafter referred to as "RhoNox-3") was synthesized as described below.

Di-tertiary-butyl-4,4'-(3-oxo-3H-spiro[isobenzofuran-1,9'-xanthene]3',6'-diyl)bis(piperazine-1-carboxylate), which is a precursor compound, was synthesized in accordance with a procedure disclosed in, for example, Org. Lett. 2011, 13, 6354-6357. 188 mg (0.028 mmol) of di-tertiary-butyl-4,4'-(3-oxo-3H-spiro[isobenzofuran-1,9'-xanthene]3',6'-diyl)bis(piperazine-1-carboxylate) was dissolved in 3 mL of methanol, and 3 mL of a 2 M HCl/methanol solution was added dropwise thereto at 0° C. The mixture was allowed to return to room temperature and stirred for hours, followed by distillation under reduced pressure to thereby obtain a residue (dark purple powder). This residue was dissolved in 5 mL of dry dichloromethane, and 196 μL (1.41 mmol) of triethylamine and 68 μL (0.84 mmol) of pyridine were added thereto. The mixture was cooled to 0° C., and a solution of 60 μL (0.28 mmol) of acetyl chloride in dichloromethane (3 mL) was added thereto. The mixture was allowed to return to room temperature and stirred in a nitrogen atmosphere for 3 hours, followed by quenching with 30 mL of a saturated sodium bicarbonate aqueous solution, and then extraction with dichloromethane (30 mL×5). The organic layer was washed with 50 mL of water and 50 mL of salt water. The obtained solution was dried over anhydrous magnesium sulfate, and the solvent was distilled off under reduced pressure. The obtained purple powder was purified by silica gel column chromatography (chloroform:methanol=20:1 to 10:1) to thereby obtain 1,1'-(4,4'-(3-oxo-3H-spiro[isobenzofuran-1,9'-xanthene]-3',6'-diyl)bis(piperazine-4,1-diyl)diethanon) as a purple powder (142 mg, yield 92%).

$^1$H NMR (CDCl$_3$, 400 MHz) δ: 8.00 (d, J=8.0 Hz, 1H), 7.65-7.60 (m, 2H), 7.17 (d, J=7.2 Hz, 1H), 6.69 (m, 2H), 6.67 (d, J=9.2 Hz, 2H), 6.61 (dd, J=8.8 Hz, 2.4 Hz, 2H), 3.77-3.76 (m, 4H), 3.66-3.61 (m, 4H), 3.26-3.22 (m, 8H), 2.15 (s, 6H).

$^{13}$C NMR (CDCl$_3$, 100 MHz) δ: 171.8, 171.7, 154.6, 152.1, 135.9, 131.0, 130.1, 129.6, 126.4, 125.8, 113.5, 111.3, 102.7, 46.9, 42.3, 21.2.

HRMS (ESI+): m/z calculated for C$_{32}$H$_{32}$N$_4$NaO$_5^+$: 575.2265. found 575.2288.

Subsequently, 133 mg (0.24 mmol) of the obtained 1,1'-(4,4'-(3-oxo-3H-spiro[isobenzofuran-1,9'-xanthene]-3',6'-diyl)bis(piperazine-4,1-diyl)diethanon) was dissolved in 4 mL of ethyl acetate and 2 mL of dichloromethane, and 46 mg (0.27 mmol) of meta-chloroperbenzoic acid was gradually added thereto at 0° C. The mixture was allowed to return to room temperature and stirred for 1 hour, followed by distillation of the solvent under reduced pressure. The obtained residue was purified by silica gel column chromatography (chloroform:methanol=20:1 to 8:1) to thereby obtain RhoNox-3 as a while powder (60 mg, yield 44%).

$^1$H NMR (CD$_3$OD, 500 MHz) δ: 8.12 (dd, J=5.2 Hz, 2.3 Hz, 1H), 8.04 (d, J=7.5 Hz, 1H), 7.78 (t, J=8.0 Hz, 1H), 7.73 (t, J=7.5 Hz, 1H), 7.65-7.62 (m, 1H), 7.20 (d, J=7.5 Hz, 1H), 6.99 (d, J=9.2 Hz, 1H), 6.88 (d, J=2.3 Hz, 1H), 6.79 (d, J=8.6 Hz, 2.3 Hz, 1H), 6.67 (d, J=9.2 Hz, 1H), 4.63 (d, J=13.8 Hz, 1H), 4.15-4.12 (m, 2H), 4.02-3.96 (m, 2H), 3.72-3.61 (m, 5H), 3.32-3.25 (m, 6H), 2.18 (s, 3H), 2.13 (s, 1H).

$^{13}$C NMR (CD$_3$OD, 125 MHz) δ: 170.5, 170.4, 169.7, 155.3, 153.1, 152.8, 152.1, 151.9, 135.5, 130.2, 129.3, 128.4, 126.3, 124.7, 123.8, 120.8, 115.2, 112.6, 109.9, 108.4, 101.8, 82.3, 66.6, 45.7, 41.1, 41.0, 36.3, 19.8, 19.7.

HRMS (ESI+): m/z calculated for C$_{32}$H$_{33}$N$_4$O$_6^+$: 569.2395. found 569.2390.

(8) 3-(Diethylamino)-N,N-diethyl-5,5-dimethyl-3'-oxo-3'H,5H-spiro[dibenzo[b,e]silyne-10,1'-isobenzofuran]-7-amine oxide (which is hereinafter referred to as "Si-RhoNox-1") was synthesized as described below.

3,7-Bis(diethylamino)-5,5-dimethyl-3'H,5H-spiro[dibenzo[b,e]silyne-10,1'-isobenzofuran]-3'-one (Si-Rhodamine), which is a precursor compound, was synthesized in accordance with a procedure disclosed in, for example, Chemical Communications 2014, 50, 14374-14377. 300 mg (0.6 mmol) of Si-rhodamine was dissolved in 15 mL of a solution of 104 mg (1.2 mmol) of sodium hydrogen carbonate in ethyl acetate, and 182 mg (0.74 mmol) of meta-chloroperbenzoic acid was gradually added thereto at 0° C. The mixture was heated to room temperature, and then stirred for 30 minutes. The insoluble substances were removed by filtration through a Celite pad, followed by distillation under reduced pressure. The obtained residue was purified by silica gel column chromatography (chloroform:methanol=15:1) to thereby obtain Si-RhoNox-1 as an orange powder (172 mg, yield 55%).

$^1$H NMR (400 MHz, CDCl$_3$) δ: 8.31 (d, 1H, J=2.4 Hz), 8.01 (d, 1H, J=7.7 Hz), 7.72 (t, 1H, J=7.0 Hz), 7.61 (t, 1H, J=7.5 Hz), 7.41 (t, 2H, J=7.5 Hz), 7.01 (d, 1H, J=9.2 Hz), 6.94 (d, 1H, J=2.9 Hz), 6.83 (d, 1H, J=9.2 Hz), 6.51 (dd, 1H, J=9.2, 2.9 Hz), 3.66-3.62 (m, 4H), 3.37 (q, 4H, J=7.1 Hz), 1.16-1.12 (m, 12H), 0.68 (d, 6H, J=14.0 Hz);

$^{13}$C NMR (100 MHz, CDC$_3$) δ: −2.12, 8.01, 8.03, 12.13, 18.11, 43.92, 66.43, 66.51, 76.89, 90.45, 112.06, 115.59, 121.67, 124.48, 125.77, 126.53, 126.64, 127.34, 128.14, 128.92, 133.53, 136.47, 138.43, 145.18, 146.49, 152.51, 169.76;

HRMS (ESI+): m/z calculated for C$_{30}$H$_{37}$N$_2$O$_3$Si$^+$: 501.2568. found 501.2571.

Test Example 1

Rhonox-1 and Polydentate Ligand Compound

This test used RhoNox-1 as a fluorescence probe. In this test, a 1 mM solution of RhoNox-1 in dimethyl sulfoxide was prepared for every specimen, and a buffer solution was added to achieve a desired final concentration.

RhoNox-1 was added to a 50 mM HEPES buffer solution (pH of 7.4) to give a final concentration of 2 μM, and polydentate ligand compounds (NTA, EDTA, and TPA) were individually further added thereto to give a final concentration of 200 M. Iron(II) sulfate was then added thereto to give a final concentration of μM, and the mixture was measured for fluorescence every 5 minutes while being stirred at room temperature. Excitation wavelength: 540 nm.

Figure 2:
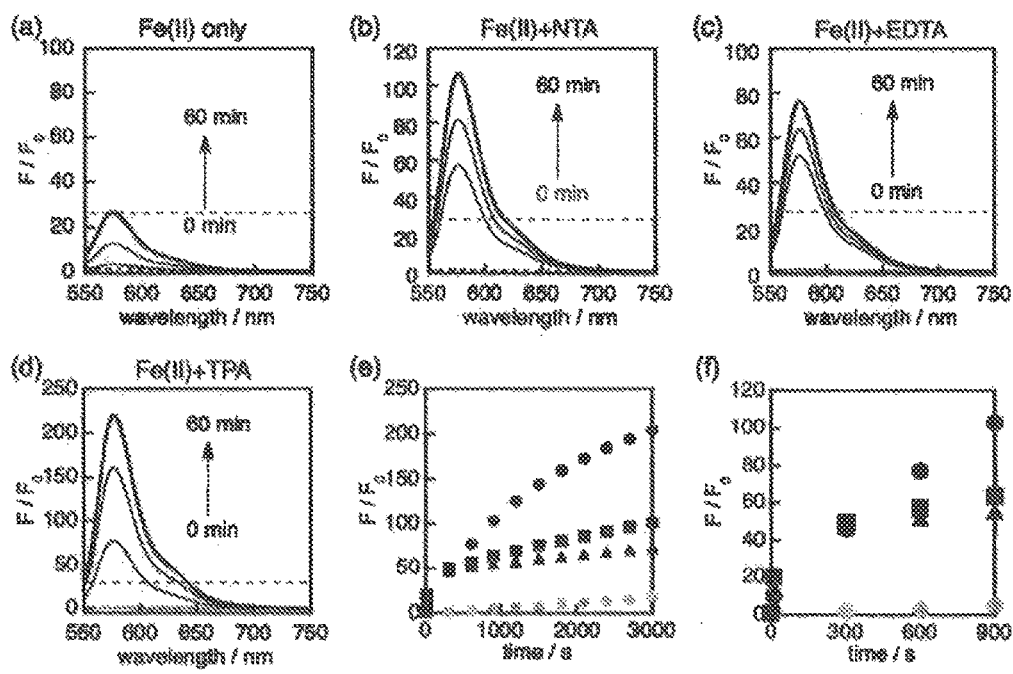
FIG. 2: Charts (a) to (d) show a change in fluorescence spectrum observed when iron(II) sulfate was added to RhoNox-1 in the presence of polydentate ligand compounds. Chart (a) shows a change in fluorescence spectrum in the absence of a polydentate ligand compound, chart (b) shows the case where NTA was present, chart (c) shows the case where EDTA was present, and chart (d) shows the case where TPA was present. The dotted line indicates the fluorescence intensity observed in 1 hour in the case where a polydentate ligand compound was absent. Chart (e) shows a change in fluorescence intensity over time at 575 nm in the spectrum change; gray circle: absence of polydentate ligand compound; solid square: NTA; solid triangle: EDTA; solid circle: TPA. Chart (f) shows an enlarged view of the part ranging from 0 to 900 seconds of chart (e). Measurement conditions: the measurement was performed with 2 µM of RhoNox-1, 20 µM of FeSO$_4$, and 200 µM of a polydentate ligand compound in 50 mM of a HEPES buffer solution (pH of 7.4). Excitation wavelength: 540 nm.

As shown in charts (a) to (d) of FIG. 2, whereas the fluorescence intensity increased about 30 times in 1 hour in the case where only Fe(II) ions were added, Fe(II) ions+NTA exhibited fluorescence intensity 100 times higher, Fe(II) ions+TPA exhibited fluorescence intensity 200 times higher, and Fe(II) ions+EDTA exhibited fluorescence intensity 80 times higher. Charts (e) and (f) of FIG. 2 revealed that the change in fluorescence intensity over time at 575 nm exhibited a significant difference in particular at the beginning; i.e., about 5 minutes after the polydentate ligand compounds were added, Fe(II) ions+NTA, Fe(II) ions+TPA, and Fe(II) ions+EDTA at once exhibited a fluorescence intensity of substantially the same level as exhibited after 1 hour by the specimen containing no polydentate ligand compound. This indicates that adding these polydentate ligand compounds enables the detection of Fe(II) ions with higher sensitivity.

Test Example 2

HMRhonox-M and NTA

This test used HMRhoNox-M as a fluorescence probe. In this test, a 1 mM solution of HMRhoNox-M in dimethyl sulfoxide was prepared for every specimen, and a buffer solution was added to achieve a desired final concentration.

HMRhoNox-M was added to 50 mM of a HEPES buffer solution (pH of 7.4) to give a final concentration of 2 µM, and then a polydentate ligand compound NTA was further added to give a final concentration of 200 µM. Iron(II) sulfate was then added thereto to give a final concentration of 20 µM, and the mixture was measured for fluorescence every 5 minutes while being stirred at room temperature. The excitation wavelength: 520 nm.

Figure 3:
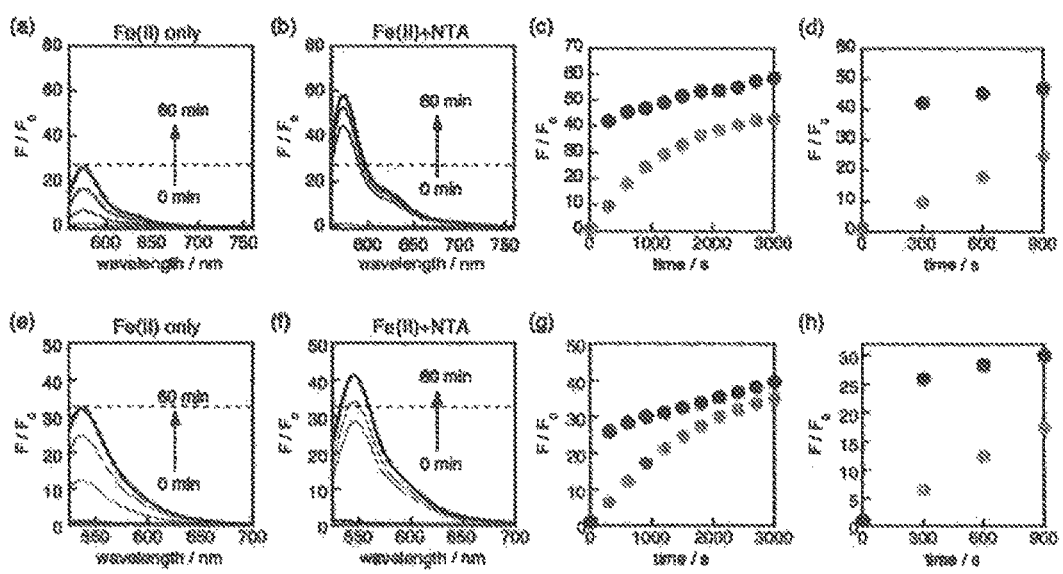
FIG. 3: Charts (a) and (b) show a change in fluorescence spectrum observed when iron(II) sulfate was added to HMRhoNox-M in the presence of NTA. Chart (a): absence of NTA. Chart (b): NTA was present. Chart (c) shows a change in fluorescence intensity over time at 575 nm in the spectrum change; gray circle: absence of NTA; solid circle: NTA. Chart (d) shows an enlarged view of the part ranging from 0 to 900 seconds of chart (c). Measurement conditions: the measurement was performed with 2 µM of HMRhoNox-M, µM of FeSO$_4$, and 200 µM of NTA in 50 mM of a HEPES buffer solution (pH of 7.4). Excitation wavelength: 550 nm. Charts (e) and (f) show a change in fluorescence spectrum observed when iron(II) sulfate was added to HMFluNox-M in the presence of NTA. Chart (e): absence of NTA; chart (f): NTA was present. Chart (g) shows a change in fluorescence intensity over time at 535 nm in the spectrum change; gray circle: absence of NTA; the solid circle: NTA was present. Chart (h) shows an enlarged view of the part ranging from 0 to 900 seconds of chart (g). Measurement conditions: the measurement was performed with 2 µM of HMFluNox-M, µM of FeSO$_4$, and 200 µM of NTA in 50 mM of a HEPES buffer solution (pH of 7.4). Excitation wavelength: 520 nm.
Figure 4:
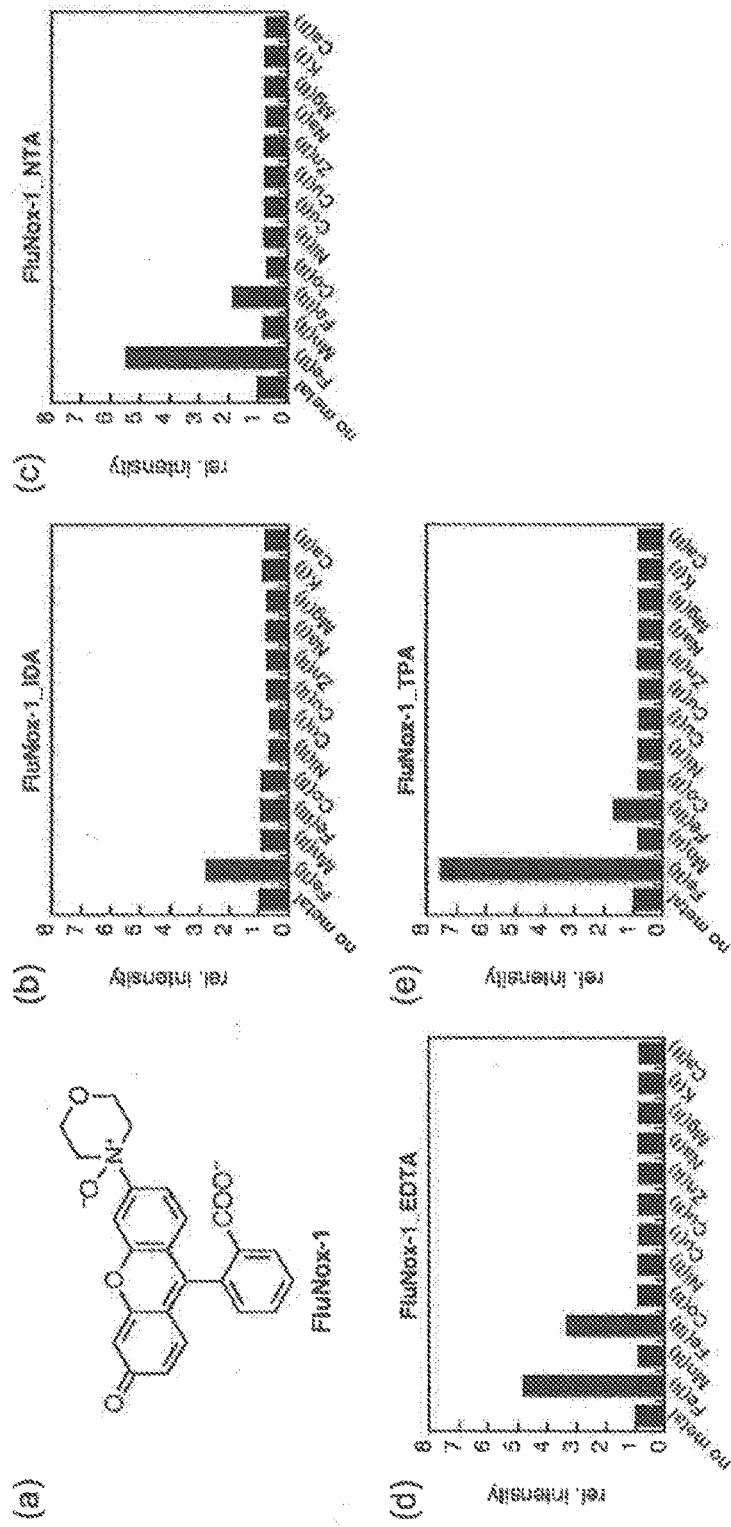
FIG. 4: Chart (a) shows the structure of FluNox-1. Charts (b) to (e) show the results obtained by adding metal compounds to FluNox-1 in the presence of polydentate ligand compounds, and 30 minutes later, measuring the fluorescence intensity with a microplate reader. The vertical axis indicates the value of fluorescence intensity relative to the "1" mark, which indicates the fluorescence intensity observed when only the fluorescence probe was added (indicated as "no metal" in the figures). In charts (b) IDA, (c) NTA, (d) EDTA, and (e) TPA, the excitation wavelength is 490 nm and the measurement wavelength is 510 to 570 nm.
Figure 5:
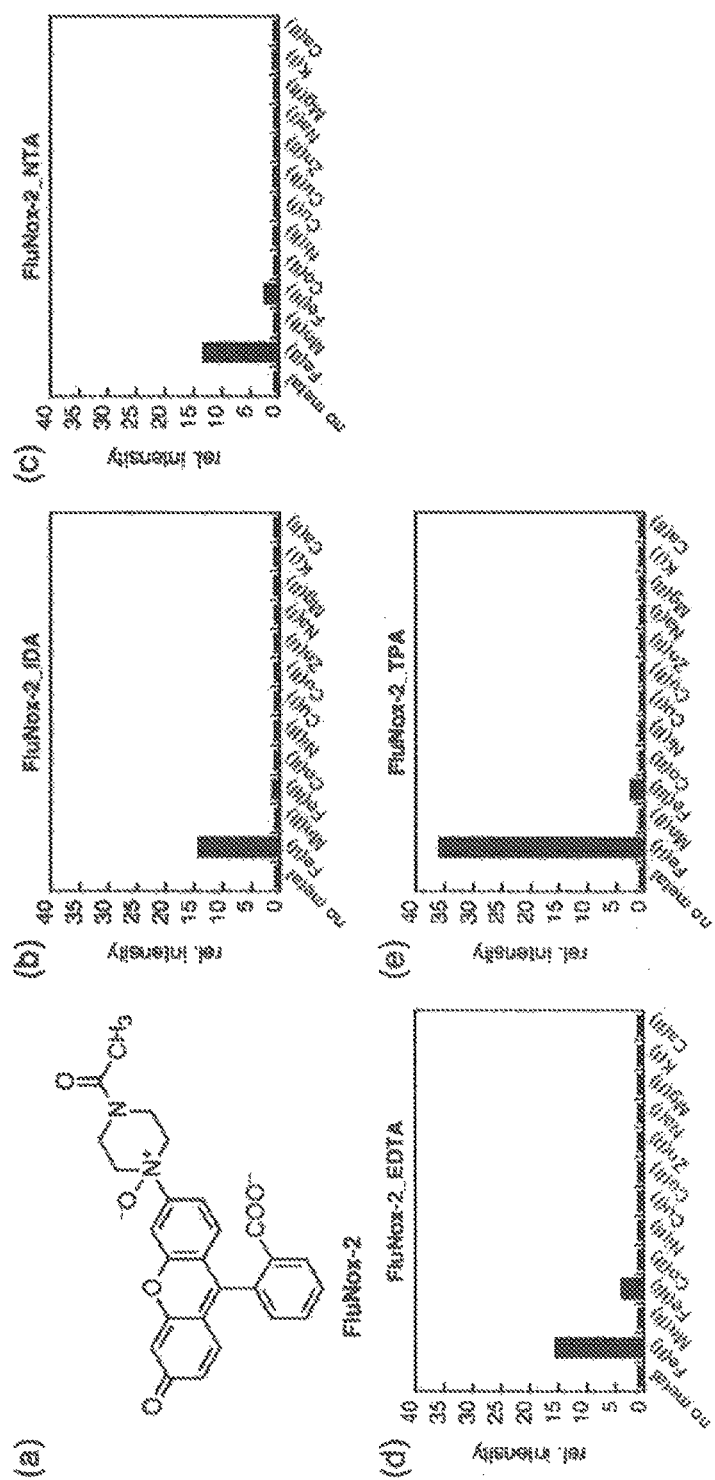
FIG. 5: Chart (a) shows the structure of FluNox-2. Charts (b) to (e) show the results obtained by adding metal compounds to FluNox-2 in the presence of polydentate ligand compounds, and 30 minutes later, measuring the fluorescence intensity with a microplate reader. The vertical axis indicates the value of fluorescence intensity relative to the "1" mark, which indicates the fluorescence intensity observed when only the fluorescence probe was added (indicated as "no metal" in the figures). In charts (b) IDA, (c) NTA, (d) EDTA, and (e) TPA, the excitation wavelength is 490 nm and the measurement wavelength is 510 to 570 nm.
Figure 6:
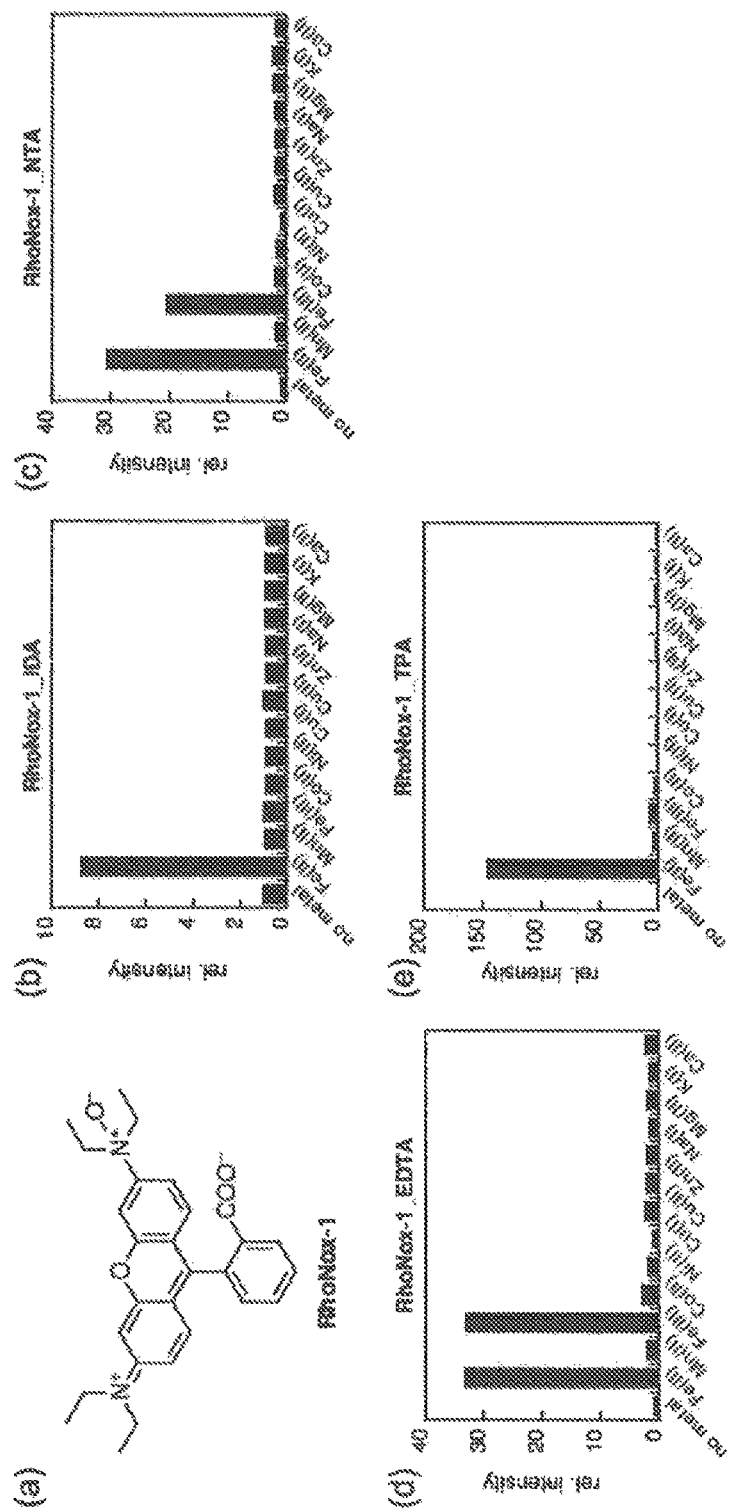
FIG. 6: Chart (a) shows the structure of RhoNox-1. Charts (b) to (e) show the results obtained by adding metal compounds to RhoNox-1 in the presence of polydentate ligand compounds, and 30 minutes later, measuring the fluorescence intensity with a microplate reader. The vertical axis indicates the value of fluorescence intensity relative to the "3" mark, which indicates the fluorescence intensity observed when only the fluorescence probe was added (indicated as "no metal" in the figures). In charts (b) IDA, (c) NTA, (d) EDTA, and (e) TPA, the excitation wavelength is 525 nm and the measurement wavelength is 580 to 640 nm.
Figure 7:
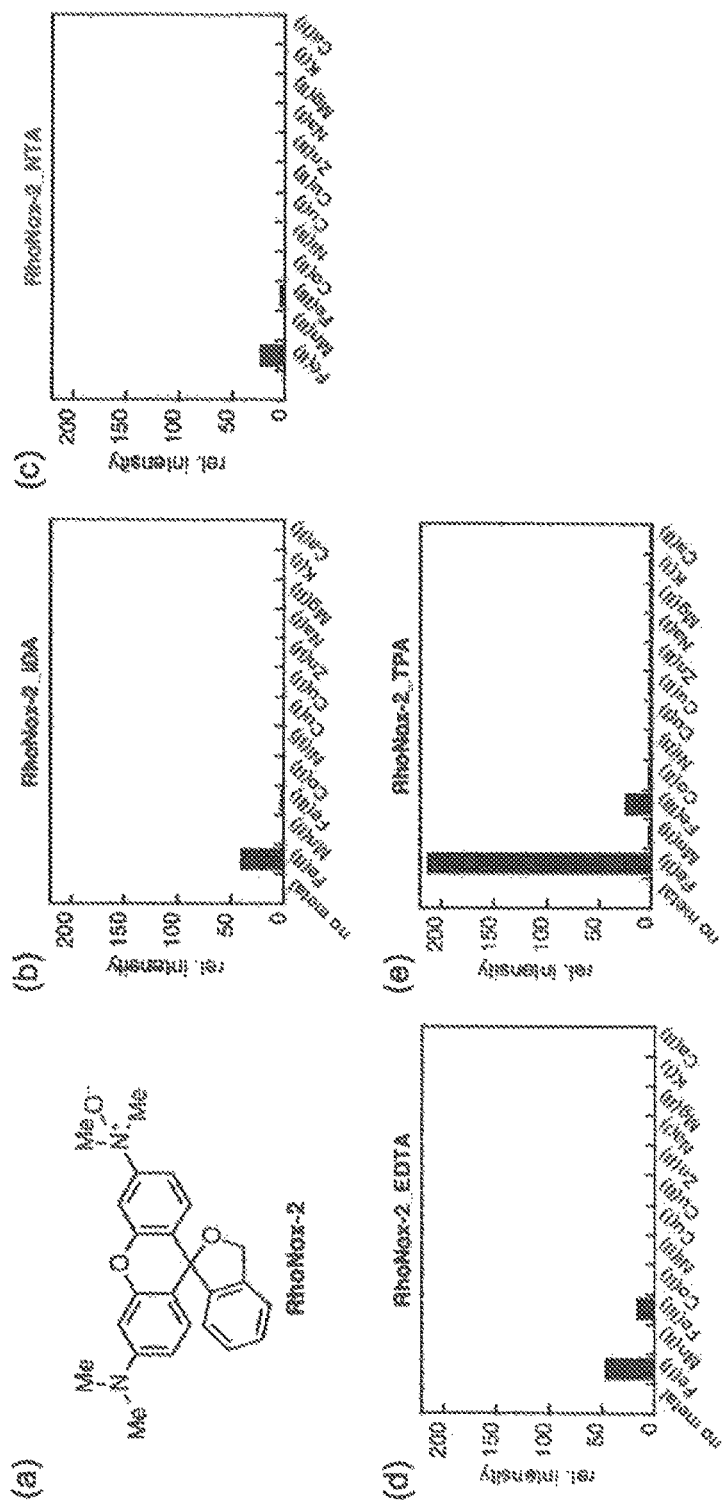
FIG. 7: Chart (a) shows the structure of RhoNox-2. Charts (b) to (e) show the results obtained by adding metal compounds to RhoNox-2 in the presence of polydentate ligand compounds, and 30 minutes later, measuring the fluorescence intensity with a microplate reader. The vertical axis indicates the value of fluorescence intensity relative to the "1" mark, which indicates the fluorescence intensity observed when only the fluorescence probe was added (indicated as "no metal" in the figures). In charts (b) IDA, (c) NTA, (d) EDTA, and (e) TPA, the excitation wavelength is 525 nm and the measurement wavelength is 580 to 640 nm.
Figure 8:
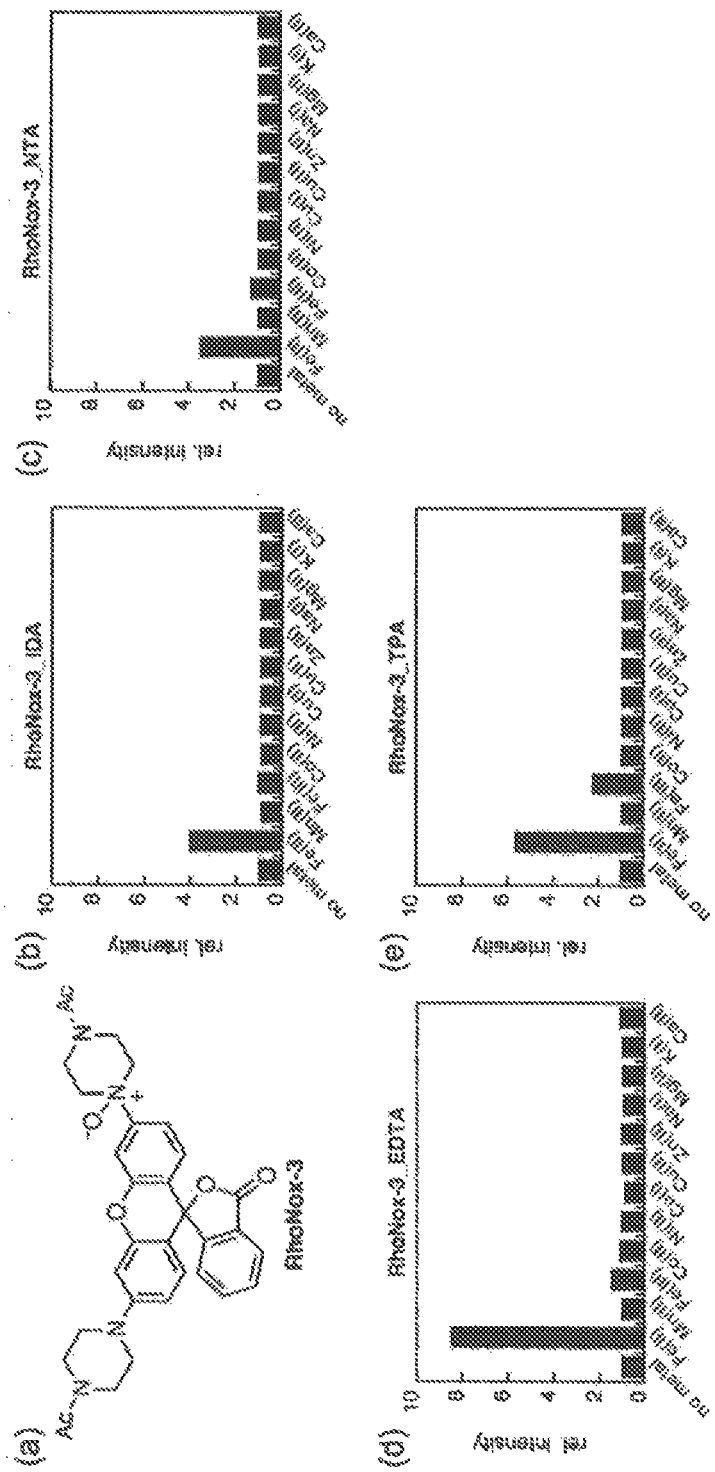
FIG. 8: Chart (a) shows the structure of RhoNox-3. Charts (b) to (e) show the results obtained by adding metal compounds to RhoNox-3 in the presence of polydentate ligand compounds, and 30 minutes later, measuring the fluorescence intensity with a microplate reader. The vertical axis indicates the value of fluorescence intensity relative to the "1" mark, which indicates the fluorescence intensity observed when only the fluorescence probe was added (indicated as "no metal" in the figures). In charts (b) IDA, (c) NTA, (d) EDTA, and (e) TPA, the excitation wavelength is 525 nm and the measurement wavelength is 580 to 640 nm.
Figure 9:
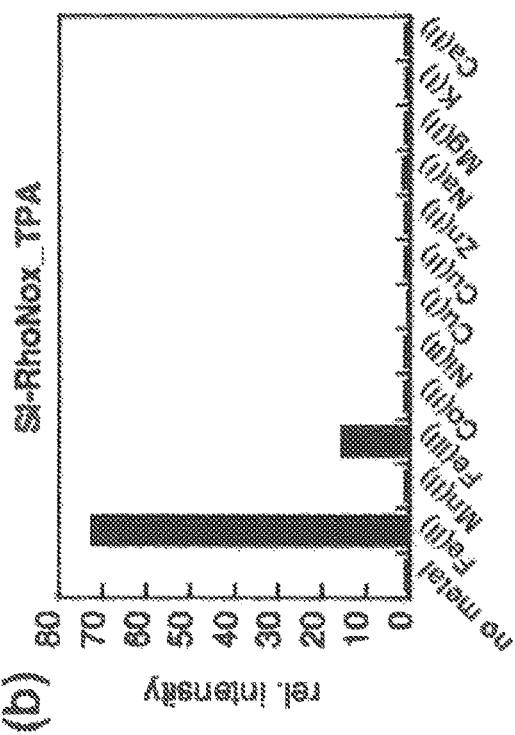
FIG. 9: Chart (a) shows the structure of Si-RhoNox-1. Chart (b) shows the results obtained by adding metal compounds to Si-RhoNox-1 in the presence of TPA, and 30 minutes later, measuring the fluorescence intensity with a microplate reader. The vertical axis indicates the value of fluorescence intensity relative to the "1" mark, which indicates the fluorescence intensity observed when only the fluorescence probe was added (indicated as "no metal" in the figures). Excitation wavelength 625 nm; measurement wavelength: 660 to 720 nm.
Figure 9:
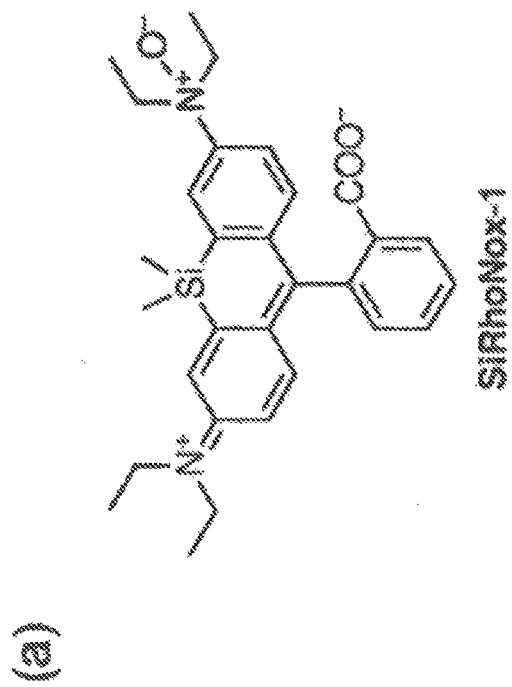

As shown in charts (a) to (d) of FIG. 3, the fluorescence measurement using hydroxymethyl-containing HMRhoNox-M in the presence of NTA revealed that Fe(II) ions can be detected with high sensitivity.

Test Example 3

HMFluNox-M and NTA

This test used HMFluNox-M as a fluorescence probe. In this test, a 1 mM solution of HMFluNox-M in dimethyl sulfoxide was prepared for every specimen, and a buffer solution was added to achieve a desired final concentration.

HMFluNox-M was added to 50 mM of a HEPES buffer solution (pH of 7.4) to give a final concentration of 2 µM, and then a polydentate ligand compound NTA was further added to give a final concentration of 200 µM. Iron(II) sulfate was then added thereto to give a final concentration of 20 µM, and the mixture was measured for fluorescence every 5 minutes while being stirred at room temperature.

As shown in charts (e) to (h) of FIG. 3, the fluorescence measurement using hydroxymethyl-containing HMFluNox-M in the presence of NTA revealed that Fe(II) ions can be detected with high sensitivity.

The experimental fact demonstrated above revealed that allowing various polydentate ligand compounds to be present together with the fluorescence probe represented by formula (I) can significantly increase both the response rate and the fluorescence intensity enhancement ratio in response to Fe(II) ions. In other words, the Fe(II) ion detection agent according to the present invention can detect Fe(II) ions contained in various specimens fast with high selectivity and high sensitivity.

Test Example 4

Selective Detection of Fe(II) Ion

This test used FluNox-1, FluNox-2, RhoNox-1, RhoNox-2, RhoNox-3, or Si-RhoNox-1 as a fluorescence probe, IDA, NTA, EDTA, or TPA as a polydentate ligand compound, and $MnSO_4$, $CoSO_4$, $NiSO_4$, $FeSO_4$, $FeCl_3$, $CuSO_4$, $ZnSO_4$, NaCl, KCl, $MgCl_2$, $CaCl_2$, or $[Cu(MeCN)_4PF_6]$ as a metal compound. First, the following stock solutions were prepared.

Metal Compound Stock Solution
Transition metal compound other than $[Cu(MeCN)_4PF_6]$:1 mM aqueous solution
Alkali metal or alkaline-earth metal compound: 100 mM aqueous solution
$[Cu(MeCN)_4PF_6]$:1 mM acetonitrile solution
Fluorescence Probe Stock Solution
1 mM Dimethyl formamide solution
Multidentate Ligand Compound Stock Solution
IDA (sodium salt): 100 mM aqueous solution
NTA (sodium salt): 100 mM aqueous solution
EDTA (sodium salt): 100 mM aqueous solution
TPA: 100 mM dimethyl sulfoxide solution These stock solutions were individually added to a buffer solution to give a desired final concentration for use. The following is the specific procedure. A fluorescence probe was added to a 50 mM HEPES buffer solution (pH of 7.4) to give a final concentration of 2 µM, and then a polydentate ligand compound was further added thereto to give a final concentration of 200 µM. 100 µL of the obtained solution was placed in each well of a 96-well plate. A transition metal compound was then added to each well to give a final concentration of 20 µM or an alkali metal or alkaline-earth metal compound was added to each well to give a final concentration of 2 mM. The mixture was incubated for 30 minutes with stirring at room temperature, and measured for fluorescence intensity with a microplate reader (GloMax, Promega Corporation). A filter set suitable for the wavelength of each fluorescence probe was used to measure the fluorescence intensity. Specifically, an excitation wavelength of 490 nm was applied for FluNox-1 and FluNox-2, and the fluorescence intensity in the range of 510 nm to 570 nm was measured. An excitation wavelength of 525 nm was applied for RhoNox-1, RhoNox-2, and RhoNox-3, and the fluorescence intensity in the range of 580 nm to 640 nm was measured. An excitation wavelength of 625 nm was applied for Si-RhoNox-1, and the fluorescence intensity in the range of 660 nm to 720 nm was measured. FIGS. 4 to 9 show the measurement results.

Test Example 5

This test used FluNox-1, FluNox-2, RhoNox-1, RhoNox-2, RhoNox-3, or Si-RhoNox-1 as a fluorescence probe, IDA, NTA, EDTA, or TPA as a polydentate ligand compound, and $FeSO_4$ as a metal compound. Stock solutions were prepared in the same manner as in Test Example 4.

Figure 10:
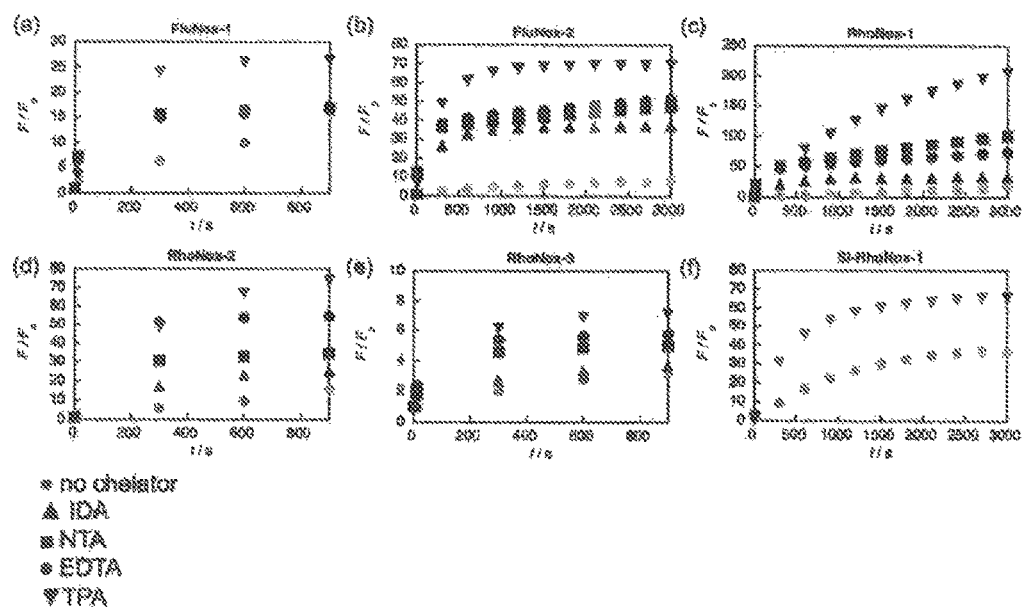
FIG. 10: Charts (a) to (f) show the results obtained by adding iron(II) sulfate to the fluorescence probes in the presence of polydentate ligand compounds, and measuring the changes in fluorescence intensity over time with a spectrofluorophotometer. The vertical axis indicates the value of fluorescence intensity relative to the "1" mark, which indicates the fluorescence intensity observed when only the fluorescence probes were added. In charts (a) FluNox-1, (b) FluNox-2, (c) RhoNox-1, (d) RhoNox-2, (e) RhoNox-3, and (f) Si-RhoNox-1, symbols indicate the following: gray circle: absence of polydentate ligand compounds; solid triangle: IDA; solid square: NTA; solid circle: EDTA; solid inverted triangle: TPA. Excitation wavelength: 500 nm (FluNox-1 and FluNox-2), 530 nm (RhoNox-1, RhoNox-2, and RhoNox-3), and 630 nm (SiRhoNox-1). Measurement wavelength: 530 nm (FluNox-1 and FluNox-2), 570 nm (RhoNox-1, RhoNox-2, and RhoNox-3), and 665 nm (SiRhoNox-1).

The stock solutions were individually added to a buffer solution to give a desired final concentration for use. The following is the specific procedure. A fluorescence probe was added to 3 mL of a 50 mM HEPES buffer solution (pH of 7.4) to give a final concentration of 2 µM, and then a polydentate ligand compound was further added thereto to give a final concentration of 200 µM. $FeSO_4$ was then added thereto to give a final concentration of 20 µM. The fluorescence spectrum of each solution was measured with a spectrofluorophotometer (FP-6600, JASCO) at a time point of 0 seconds, 10 seconds, and then every 300 seconds over 60 minutes after the addition. The excitation wavelength was 500 nm for FluNox-1 and FluNox-2, 530 nm for RhoNox-1, RhoNox-2, and RhoNox-3, and 630 nm for SiRhoNox-1. The fluorescence intensity at 530 nm (FluNox-1 and FluNox-2), 570 nm (RhoNox-1, RhoNox-2, and RhoNox-3), and 665 nm (SiRhoNox-1) was measured. FIG. 10 shows the measurement results.

We claim:
1. An Fe(II) ion detection agent comprising a compound represented by formula (I):

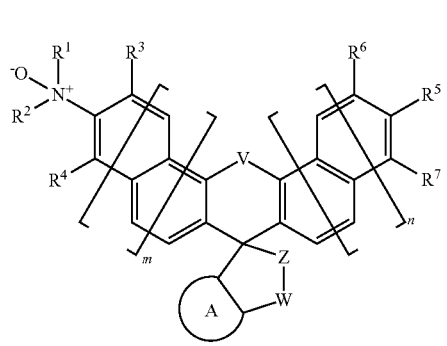

wherein
R¹ and R² are the same or different and represent lower alkyl, carboxy lower alkyl, aryl, or aryl lower alkyl;
R³ and R⁴ are the same or different and represent hydrogen, halogen, or lower alkyl;
R¹ and R² are optionally taken together with the nitrogen atom to which they are attached to form a pyrrolidine ring, a piperidine ring, a morpholine ring, or an optionally substituted piperazine ring;
R¹ and R³ are optionally taken together to form trimethylene;
R² and R⁴ are optionally taken together to form trimethylene;
R⁵ represents optionally protected hydroxyl, lower alkoxy, or a group represented by formula (A): —NR⁵¹R⁵² wherein R⁵¹ and R⁵² are the same or different and represent lower alkyl, carboxy lower alkyl, aryl, or aryl lower alkyl, or R⁵¹ and R⁵² are optionally taken together with the nitrogen atom to which they are attached to form a pyrrolidine ring, a piperidine ring, a morpholine ring, or an optionally substituted piperazine ring;
R⁶ and R⁷ are the same or different and represent hydrogen, halogen, or lower alkyl;
when R⁵ is the group represented by formula (A), R⁵¹ and R⁶ are optionally taken together to form trimethylene, or R⁵² and R⁷ are optionally taken together to form trimethylene;
ring A represents an optionally substituted aromatic ring or an optionally substituted heteroaromatic ring;
V represents 0 or SiR¹⁰R¹¹ wherein R¹⁰ and R¹¹ are the same or different and represent hydrogen or lower alkyl;
W represents CH₂, CO, or S(O)$_p$;
Z represents O or NR⁹ wherein R⁹ represents hydrogen or alkyl;
m and n are the same or different and represent 0 or 1; and
p represents 1 or 2,
in combination with a second compound selected from iminodiacetic acid (IDA), nitrilotriacetic acid (NTA), N,N,N',N'-ethylenediaminetetraacetic acid (EDTA), 1,3-propanediamine tetraacetic acid (PDTA), diethylenetriamine pentaacetic acid (DTPA), hydroxyethyl ethylenediamine triacetic acid (HEDTA), triethylenetetraaminehexaacetic acid (TTHA), 1,2-diaminocyclohexane tetraacetic acid (CyDTA), glycol ether diamine tetraacetic acid (GEDTA or EGTA), N,N-bis (2-hydroxybenzyl) ethylenediamine diacetic acid (HBED), ethylenediamine dipropionic acid (EDDP), ethylenediamine diacetic acid (EDDA), ethylenediamine disuccinic acid (EDDS), 1,3-diamino-2-hydroxypropane tetraacetic acid (DPTA-OH), dihydroxyethyl glycine (DHEG), hexamethylenediamine tetraacetic acid (HDTA), hydroxyethyl iminodiacetic acid (HIDA), diaminopropane tetraacetic acid(methyl-EDTA), nitrilotripropionic acid (NTP), L-glutamic acid diacetic acid (GLDA), O,O'-bis-2-aminophenyl-N,N, N',N'-tetraacetic acid (BAPTA), ethylenediamine tetrakis(methylene phosphonic acid) (EDTPO), nitrilotris (methylene phosphonic acid) (NTPO), hydroxyethylidene diphosphonic acid (HEDP), phosphonobutane tricarboxylic acid (PBTC), tris(2-pyridylmethyl)amine (TPA), dipicolylamine (DPA), o-aminophenol-N,N,O-triacetic acid (APTRA), porphyrin or its derivative, phthalocyanine or its derivative, 1,4,7-triazacyclononane (TACN), 1,4,7,10-tetraazacyclo-dodecane (CYCLEN), and 1,4,8,11-tetraazacyclo-tetradecane (CYCLAM), or a salt thereof.

2. The Fe(II) ion detection agent according to claim 1, wherein ring A in formula (I) is represented by formula (a):

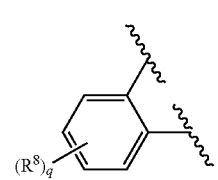

wherein R⁸ represents optionally protected hydroxyl, lower alkoxy, halogen, carboxyl, lower alkoxycarbonyl, —N=C=O, —N=C=S, sulfo, or active ester; q represents 0, 1, 2 or 3; and when q is 2 or 3, R⁸ is the same or different.

3. The Fe(II) ion detection agent according to claim 1, wherein R¹ and R² are the same or different and represent C$_{1-6}$ alkyl;
R¹ and R² are optionally taken together with the nitrogen atom to which they are attached to form a morpholine ring, or an optionally substituted piperazine ring;
R³ and R⁴ represents hydrogen, or
R¹ and R³ are optionally taken together to form trimethylene;
R² and R⁴ are optionally be taken together to form trimethylene;
R⁵ represents optionally protected hydroxyl or a group represented by formula (A): —NR⁵¹R⁵²; when
R⁵ is the group represented by formula (A), R⁵¹ and R⁵² are the same or different and represent C$_{1-6}$ alkyl;
R⁶ and R⁷ represent hydrogen; or
R⁵¹ and R⁶ are optionally taken together to form trimethylene;
R⁵² and R⁷ are optionally be taken together to form trimethylene;
W is CH₂ or CO; Z is O; m is 0; and n is 0.

4. The Fe(II) ion detection agent according to claim 1, wherein R¹ and R² are the same or different and represent C$_{1-3}$ alkyl; R³ and R⁴ represent hydrogen; R⁵ represents optionally protected hydroxyl or a group represented by formula (A): —NR⁵¹R⁵²; when R⁵ is the group represented by formula (A), R⁵¹ and R⁵² are the same or different and represent C$_{1-3}$ alkyl; R⁶ and R⁷ represent hydrogen; W is CH₂ or CO; Z is O; m is 0; and n is 0.

5. The Fe(II) ion detection agent according to claim 1, wherein the compound represented by formula (I) and the second compound are mixed.

6. The Fe(II) ion detection agent according to claim 1 that is in the form of a kit comprising a container containing the compound represented by formula (I) and a container containing the second compound.

7. A method for detecting Fe(II) ions, comprising the steps of:
(1) mixing a specimen containing Fe(II) ions with the Fe(II) ion detection agent according to claim 1 to obtain a mixture; and
(2) measuring a fluorescence spectrum of the obtained mixture.

8. A method for increasing detection sensitivity to Fe(II) ions, comprising the steps of:
(1) mixing a specimen containing Fe(II) ions with the Fe(II) ion detection agent according to claim 1 to obtain a mixture; and
(2) measuring a fluorescence spectrum of the obtained mixture.

9. A method for producing an Fe(II) ion detection agent, comprising the step of:
mixing a compound represented by formula (I):

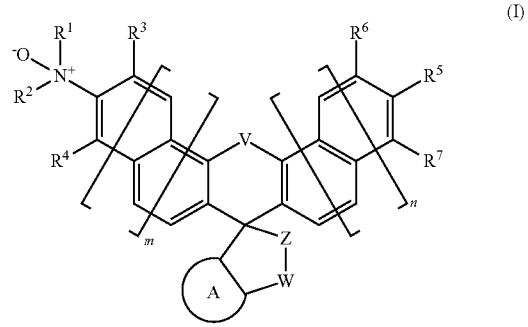

wherein
$R^1$ and $R^2$ are the same or different and represent lower alkyl, carboxy lower alkyl, aryl, or aryl lower alkyl;
$R^3$ and $R^4$ are the same or different and represent hydrogen, halogen, or lower alkyl;
$R^1$ and $R^2$ are optionally taken together with the nitrogen atom to which they are attached to form a pyrrolidine ring, a piperidine ring, a morpholine ring, or an optionally substituted piperazine ring;
$R^1$ and $R^3$ are optionally taken together to form trimethylene;
$R^2$ and $R^4$ are optionally taken together to form trimethylene;
$R^5$ is optionally protected hydroxyl, lower alkoxy, or a group represented by formula (A): $-NR^{51}R^{52}$ wherein $R^{51}$ and $R^{52}$ are the same or different and represent lower alkyl, carboxy lower alkyl, aryl, or aryl lower alkyl, or $R^{51}$ and $R^{52}$ is taken together with the nitrogen atom to which they are attached to form a pyrrolidine ring, a piperidine ring, a morpholine ring, or an optionally substituted piperazine ring;
$R^6$ and $R^7$ are the same or different and represent hydrogen, halogen, or lower alkyl;
when $R^5$ is the group represented by formula (A), $R^{51}$ and $R^6$ are optionally taken together to form trimethylene, or $R^{52}$ and $R^7$ are optionally taken together to form trimethylene;
ring A represents an optionally substituted aromatic ring or an optionally substituted heteroaromatic ring;
V represents O or $SiR^{10}R^{11}$ wherein $R^{10}$ and $R^{11}$ are the same or different and represent hydrogen or lower alkyl;
W represents $CH_2$, CO, or $S(O)_p$;
Z represents O or $NR^9$ wherein $R^9$ represents hydrogen or alkyl;
m and n are the same or different and represent 0 or 1; and
p represents 1 or 2,
with compound selected from iminodiacetic acid (IDA), nitrilotriacetic acid (NTA), N,N,N',N'-ethylenediaminetetraacetic acid (EDTA), 1,3-propanediamine tetraacetic acid (PDTA), diethylenetriamine pentaacetic acid (DTPA), hydroxyethyl ethylenediamine triacetic acid (HEDTA), triethylenetetraaminehexaacetic acid (TTHA), 1,2-diaminocyclohexane tetraacetic acid (CyDTA), glycol ether diamine tetraacetic acid (GEDTA or EGTA), N,N-bis(2-hydroxybenzyl) ethylenediamine diacetic acid (HBED), ethylenediamine dipropionic acid (EDDP), ethylenediamine diacetic acid (EDDA), ethylenediamine disuccinic acid (EDDS), 1,3-diamino-2-hydroxypropane tetraacetic acid (DPTA-OH), dihydroxyethyl glycine (DHEG), hexamethylenediamine tetraacetic acid (HDTA), hydroxyethyl iminodiacetic acid (HIDA), diaminopropane tetraacetic acid(methyl-EDTA), nitrilotripropionic acid (NTP), L-glutamic acid diacetic acid (GLDA), O,O'-bis-2-aminophenyl-N,N,N',N'-tetraacetic acid (BAPTA), ethylenediamine tetrakis(methylene phosphonic acid) (EDTPO), nitrilotris(methylene phosphonic acid) (NTPO), hydroxyethylidene diphosphonic acid (HEDP), phosphonobutane tricarboxylic acid (PBTC), tris (2-pyridylmethyl)amine (TPA), dipicolylamine (DPA), o-aminophenol-N,N,O-triacetic acid (APTRA), porphyrin or its derivative, phthalocyanine or its derivative, 1,4,7-triazacyclononane (TACN), 1,4,7,10-tetra-azacyclo-dodecane (CYCLEN), and 1,4,8,11-tetra-azacyclo-tetradecane (CYCLAM), or a salt thereof.

* * * * *